United States Patent
Moller et al.

(10) Patent No.: US 11,499,184 B2
(45) Date of Patent: Nov. 15, 2022

(54) CIRCULATING SERUM MICRORNA BIOMARKERS AND METHODS

(71) Applicant: St. John's University, Queens, NY (US)

(72) Inventors: Simon Geir Moller, Queens, NY (US); Indranil Basak, Queens, NY (US); Ketan Patil, Queens, NY (US); Jan Petter Larsen, Queens, NY (US)

(73) Assignee: ST. JOHN'S UNIVERSITY, Queens, NY (US)

( * ) Notice: Subject to any disclaimer, the term of this patent is extended or adjusted under 35 U.S.C. 154(b) by 45 days.

(21) Appl. No.: 16/075,354

(22) PCT Filed: Feb. 3, 2017

(86) PCT No.: PCT/US2017/016412
§ 371 (c)(1),
(2) Date: Aug. 3, 2018

(87) PCT Pub. No.: WO2017/136662
PCT Pub. Date: Aug. 10, 2017

(65) Prior Publication Data
US 2020/0354768 A1  Nov. 12, 2020

Related U.S. Application Data

(60) Provisional application No. 62/291,619, filed on Feb. 5, 2016.

(51) Int. Cl.
*C12Q 1/686* (2018.01)
*C12Q 1/6883* (2018.01)

(52) U.S. Cl.
CPC ........... *C12Q 1/686* (2013.01); *C12Q 1/6883* (2013.01); *C12Q 2600/158* (2013.01); *C12Q 2600/178* (2013.01)

(58) Field of Classification Search
CPC .......... C12Q 2600/158; C12Q 2600/17; C12Q 2600/178
See application file for complete search history.

(56) References Cited

U.S. PATENT DOCUMENTS

2015/0275299 A1* 10/2015 Xu .................. C12N 15/113
514/44 A

FOREIGN PATENT DOCUMENTS

| WO | 2013/036936 A1 | 3/2013 |
| WO | 2014/018650 | 1/2014 |
| WO | 2014/075822 | 5/2014 |
| WO | 2015/091892 | 6/2015 |

OTHER PUBLICATIONS

Hunt, E.A. et al., MicroRNA Detection: Current Technology and Research Strategies, Annu. Rev. Anal. Chem., vol. 8, pp. 217-237 (Year: 2015).*
Burgos, K. et al., PLOS ONE, vol. 9, e94839, supplementa material pp. 1-13 (Year: 2014).*
Acharya, S. et al., Non-Coding RNAs in the Brain-Heart Axis: The case of Parkinson's Disease, Int. J. Mol. Sci., vol. 21, 6513, pp. 1-27 (Year: 2020).*
Leshkovitz, D. et al., Differences in microRNA detection levels are technology and sequence dependent, RNA, vol. 19, pp. 527-538 (Year: 2013).*
Alvarez-Erviti et al., "Lysosomal dysfunction increases exosome-mediated alpha synuclein release and transmission" Neurobiology of Disease, vol. 42 (2011) 360 67.
Bartel, "MicroRNAs: Genomics, Biogenesis, Mechanism, and Function", Cell, vol. 116 (2004) 281-97.
Burgos, et al., "Profiles of Extracellular miRNA in Cerebrospinal Fluid and Serum from Patients with Alzheimer's and Parkinson's Diseases Correlate with Disease Status and Features of Pathology", PLOS ONE, vol. 9, No. 5 (2014) 94839.
Carthew, et al., "Origins and Mechanisms of miRNAs and siRNAs", Cell, vol. 136, No. 4 (2009) 642-55.
Chen et al., "Characterization of microRNAs in serum: a novel class of biomarkers for diagnosis of cancer and other diseases", Cell Research, vol. 18 (2008) 997-1006.
Grasso et al., "Circulating miRNAs as Biomarkers for Neurodegenerative Disorders", Molecules, vol. 19 (2014) 6891-910.
Gregory et al., "The Microprocessor complex mediates the genesis of microRNAs", Nature, vol. 432 (2004) 235-40.
Han et al., "The Drosha—DGCR8 complex in primary microRNA processing", Genes & Development, vol. 18 (2004) 3016-20.
Kim et al., "Biogenesis of small RNAs in animals", Nature, vol. 126 (2009) 126-39.
Koval et al., "Method for widespread microRNA-155 inhibition prolongs survival in ALS-model mice", Human Molecular Genetics, vol. 22, No. 20 (2013) 4127-35.
Lee et al., "The nuclear RNase III Drosha initiates microRNA processing", Nature, vol. 425 (2003) 415-19.
MacRae et al., "In vitro reconstitution of the human RISC-loading complex", PNAS, vol. 105, No. 2 (2008) 512-17.
Saghazadeh, et al., "MicroRNA machinery in Parkinson's disease: a platform for neurodegenerative diseases", Expert Rev. Eurother. (2015) 1-27.
Shinde, et al., "Biofluid-based microRNA Biomarkers for Parkinson's Disease: an Overview and Update" vol. 2, Issue 1 (2015) 15-25.
Siomi et al., "Posttranscriptional Regulation of MicroRNA Biogenesis in Animals" Molecular Cell, vol. 38 (2010) 323-32.
The Norwegian ParkWest study (http://www.parkvest.no) http://www.ufbi.umu.se/english/collaborations/current-projects/nypum/.
National Institute of Neurological Disorders and Stroke (http://www.ninds.nih.gov/disorders/parkinsons_disease/parkinsons_disease.htm).
Affymetrix GeneChip® miRNA 4.0 Array by the Yale Center for Genome Analysis (http://medicine.yale.edu/keck/ycga/index.aspx).

(Continued)

Primary Examiner — Teresa E Strzelecka
(74) Attorney, Agent, or Firm — Venable LLP

(57) ABSTRACT

Biomarkers and methods for identifying, verifying and confirming circulating serum-based microRNAs. The microRNAs (PARKmiRs) can be used to differentiate patient's suffering from Parkinson's disease (PD) from non-PD patients.

6 Claims, 18 Drawing Sheets

Specification includes a Sequence Listing.

(56) References Cited

OTHER PUBLICATIONS

Botta-Orfila, Teresa, Identification of Blood Serum Micro-RNAs Associated With Idiopathic and LRRK2 Parkinson's Disease, Journal of Neuroscience Research, vol. 92 (2014) 1071-77.

* cited by examiner

CIRCULATING SERUM MICRORNA BIOMARKERS AND METHODS

This application is a national phase of PCT Application No. PCT/US2017/016412 filed Feb. 3, 2017, which in turn is claims benefit of U.S. Provisional Application No. 62/291,619 filed Feb. 5, 2016.

BACKGROUND OF THE INVENTION

1. Field of the Invention

The present invention generally relates to serum-based microRNAs and methods for differentiating patients suffering from Parkinson's disease, as well as assisting clinicians to determine treatment protocols for such patients.

2. Brief Description of the Background Art

Parkinson's Disease (PD) is a highly specific degeneration of dopamine-containing cells of the substantia nigra of the midbrain, causing a dopamine deficiency in the striatum. PD currently affects about 10 million people world-wide. Effective management of a patient with PD is possible in the first 5-7 years of treatment, after which time a series of often debilitating complications, together referred to as Late Motor Fluctuations (LMF) occur. It is believed that treatment with levodopa ((−)-L-α-amino-beta-(3,4-dihydroxybenzene) propanoic acid), or L-dopa, the most effective antiparkinson drug, may facilitate or even promote the appearance of LMF. Dopamine agonists are employed as a treatment alternative, but they do not offer the same degree of symptomatic relief to patients as L-dopa does.

Symptomatic therapies improve signs and symptoms without affecting the underlying disease state. Levodopa increases dopamine concentration in the striatum, especially when its peripheral metabolism is inhibited by a peripheral decarboxylase inhibitor (PDI). Levodopa/PDI therapy is widely used for symptomatic therapy for Parkinson's disease, such as combinations with levodopa, with carbidopa ((−)-L-α-hydrazino-α-methyl-beta-(3,4-dihydroxybenzene) propanoic acid monohydrate), levodopa and controlled release carbidopa, levodopa and benserazide, levodopa plus controlled release benserazide (2-Amino-3-hydroxy-propionic acid N'-(2,3,4-trihydroxy-benzyl)-hydrazide).

Catechol-O-methyltransferase (COMT) inhibitors enhance levodopa treatment as they inhibit levodopa's metabolism, enhancing its bioavailability and thereby making more of the drug available in the synaptic cleft for a longer period of time. Examples of COMT inhibitors include tolcapone (3,4-dihydroxy-4'-methyl-5-nitrobenzophenone) and entacapone ((E)-2-cyano-3-(3,4-dihydroxy-5-nitrophenyl)-N,N-diethyl-2-propenamide).

Dopamine agonists provide symptomatic benefit by directly stimulating post-synaptic striatal dopamine receptors. Examples include bromocriptine ((5α)-2-Bromo-12'-hydroxy-2'-(1-methylethyl)-5'-(2-methylpropyl)erg-otaman-3',6',18-trione), pergolide (8B-[(Methylthio)methyl]-6-propylergoline), ropinirole (4-[2-(Dipropylamino)ethyl]-1,3-dihydro-2H-indol-2-one), pramipexole ((S)-4,5,6,7-Tetrahydro-$N^6$-propyl-2,6-benzothiazolediamine), lisuride (N'-[(8a)-9,10-didehydro-6-methylergolin-8-yl]-N,N-diethyl-urea), cabergoline ((8β)-N-[3-(Dimethylamino)propyl]-N-[(ethylamino)carbonyl]-6-(2-propenyl)ergoline-8-carboxamide), apomorphine ((6aR)-5,6,6a,7-Tetrahydro-6-methyl-4H-dibenzo[de,g]quinoline-10,11-diol), sumanirole (5-(methylamino)-5,6-dihydro-4H-imidazo{4,5,1-ij}quinolin-2(1H)-one), rotigotine ((−)(S)-5,6,7,8-tetrahydro-6-[propyl[2-(2-thienyl)ethyl]amino]-1-naphthol-), talipexole (5,6,7,8-Tetrahydro-6-(2-propenyl)-4H-thiazolo[4,5-d]azepin-2-amine), and dihydroergocriptine (ergotaman-3',6',18-trione,9,10-dihydro-12'-hydroxy-2'-methyl-5'-(phenylmethyl) (5' cc)). Dopamine agonists are effective as monotherapy early in the course of Parkinson's disease and as an adjunct to levodopa in more advanced stages. Unlike levodopa, dopamine agonists directly stimulate post-synaptic dopamine receptors. They do not undergo oxidative metabolism and are not thought to accelerate the disease process.

Amantidine (1-Aminotricyclo $(3,3,1,1^{3,7})$ decane) is an antiviral agent that was discovered by chance to have anti-Parkinsonian activity. Its mechanism of action in PD has not been established, but is believed to work by increasing dopamine release. Patients who receive amantidine either as monotherapy or in combination with levodopa show improvement in akinesia, rigidity and tremor.

Other medications used in the treatment of Parkinson's disease include MAO-B inhibitors. Inhibition of L-dopa metabolism through inactivation of the monoamino oxidase type B (MAO-B) is an effective means of enhancing the efficacy of both endogenous residual dopamine and that exogenously derived from its precursor, L-dopa. Selegiline (methyl-(1-methyl-2-phenyl-ethyl)-prop-2-ynyl-amine) is a MAO-B inhibitor. There is evidence that treatment with selegiline may slow down disease progression in PD by blocking formation of free radicals derived from the oxidative metabolism of dopamine. Other examples of MAO B inhibitors include lazabemide (N-(2-Aminoethyl)-5-chloro-2-pyridinecarboxamide), rasagiline (N-propargyl-1-(R)aminoindan and caroxazone (2-oxo-2H-1,3-benzoxazine-3 (4H)-acetamide).

It is imperative to diagnose individuals with PD at an early stage to increase the efficacy of therapeutic agents. However, there are neither any objective tests nor established biomarkers for diagnosing PD. Moreover, the heterogeneity, subtypes and progression of the disease make it difficult to develop specific therapeutic candidates.

MicroRNAs ("miRNAs") are a class of non-coding RNAs that play key roles in the regulation of gene expression. miRNAs act at the post-transcriptional level and fine-tune the expression of as much as 30% of all mammalian protein-encoding genes. Mature miRNAs are short, single-stranded RNA molecules approximately 22 nucleotides in length. miRNAs may be encoded by multiple loci, and may be organized in tandemly co-transcribed clusters. miRNA genes are transcribed by RNA polymerase II as large primary transcripts (pri-microRNA) that are processed by a protein complex containing the RNase III enzyme Drosha, DGCR8 and other cofactors, to form an approximately 70 nucleotide precursor microRNA (pre-miRNA). (Cathew R W, Cell, 2009; Kim V N, Nat Rev Mol Cel Biol, 2009; Siomi H, Mol Cel, 2010; Bartel D P, Cell, 2004; Lee Y, Nature 2003; Han J, Genes Dev, 2004.) Pre-miRNA is transported to the cytoplasm by Exportin-5 where it is processed by DICER, a second RNase III enzyme, together with TRBP, PACT and Ago2 in the RNA Induced Silencing Complex resulting in miRNA duplexes (Kim V N, Nat Rev Mol Cel Biol, 2009; Gregory R I, Nature 2004; MAcRae IJ, PNAS, 2008). The guide strands of miRNA duplexes separate and associate with Ago 2 for incorporation into a ribonuclear particle to form the RNA-induced silencing complex RISC that mediates gene silencing. The mechanisms of miRNA range from direct degradation or silencing of mRNA and repression of translation to post-transcriptional upregulations. (MacRae IJ, PNAS, 2008.)

The presence of miRNAs has been reported in body fluids including blood, cerebrospinal fluid (CSF), plasma, serum and saliva at detectable levels. The tissue-specificity of miRNAs suggests their vital and integral role in various physiological processes. The tissue-enrichment promises a new but less explored role as diagnostic biomarker and potential therapeutic target. Circulating miRNAs are understood to originate from passive leakage from damaged tissue as a result of cell lysis or apoptosis, active transport from cells via microvesicles, such as exosomes, or bound within RISC protein complexes (Etheridge et al, 2011). Exosome and osmotic pump-mediated delivery of small RNA molecules to the brain and CNS, respectively, provides a solution to overcoming the limitations of miRNA-based therapies (Alvarez-Erviti et al., 2011; Koval et al, 2013, Hum. Mol. Gen). miRNA has been demonstrated to be exceptionally stable and thus present as powerful candidates to be potential biomarkers (Chen et al, 2008; Grasso, 2014).

SUMMARY OF THE INVENTION

It is an object of the present invention to identify miRNAs relevant to patients suffering from Parkinson's disease.

It is another object of the present invention to provide methods for determining patients suffering from Parkinson's disease.

These objects and others are achieved by the present invention, which provides miRNA biomarkers that may be used singly, in pairs or in combination to determine patients suffering from Parkinson's disease.

DETAILED DESCRIPTION OF THE INVENTION

Methods

Serum Samples Handling and Classification

Figure 1:
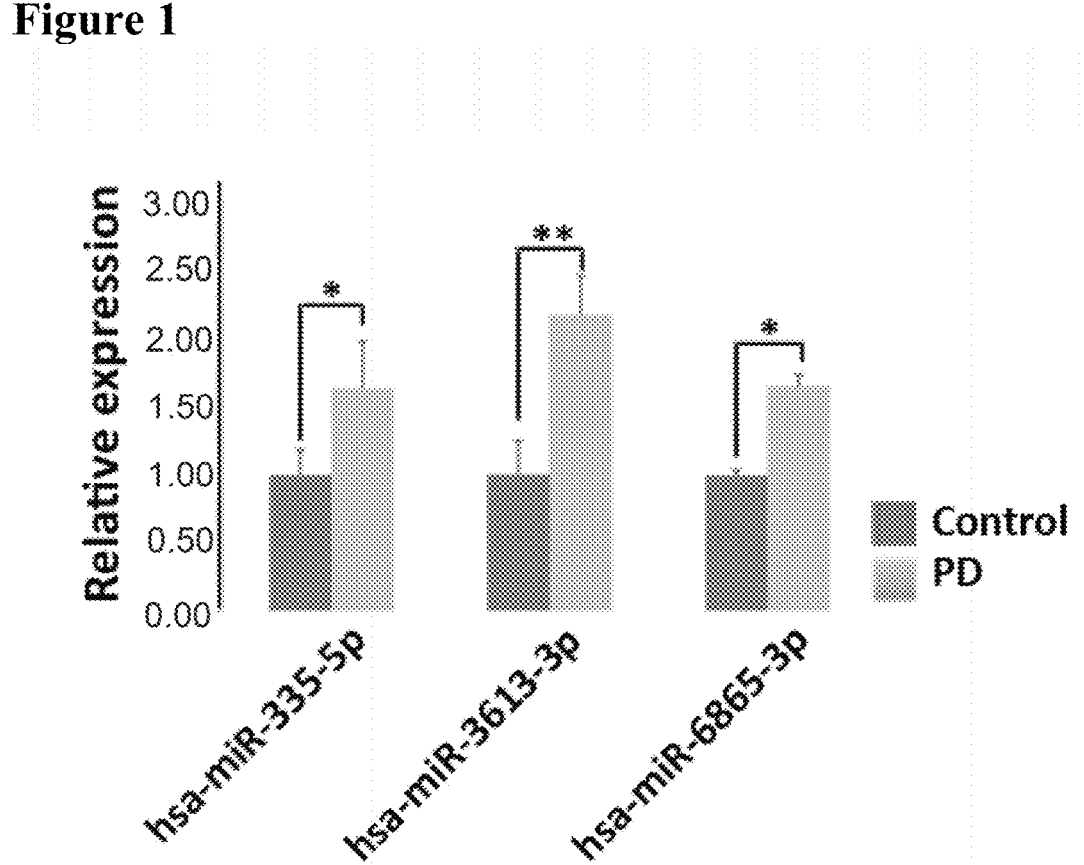
FIG. 1 shows the mean fold change of three PARKmiRNAs between PD patients and healthy controls.

All patients and controls participated in the Norwegian ParkWest project or the Swedish NYPUM study, which are ongoing prospective population-based longitudinal cohort studies investigating the incidence, neurobiology and prognosis of PD. The Norwegian ParkWest study is a prospective longitudinal multicenter cohort study of patients with incident Parkinson's disease (PD) from Western and Southern Norway. Between Nov. 1, 2004 and 31st of Aug. 2006 it was endeavored to recruit all new cases of Parkinson Disease within the study area. Since the start of the study 212 of 265 (80%) of these patients and their age-/sex-matched control group have been followed. Further information about this project can be found at http://www.parkvest.no. The NYPUM study began in 2004 and endeavours to identify all new cases with idiopathic parkinsonism within the Umeå catchment area and follow them in their disease progression for at least five years. Further information about this study can be found at http://www.ufbi.umu.se/english/collaborations/current-projects/nypum/.

All possible efforts were undertaken to establish an unselected and population-representative cohort of patients with PD. Patients were included if they had provided serum at study entry and fulfilled diagnostic criteria for PD of the National Institute of Neurological Disorders and Stroke (http://www.ninds.nih.gov/disorders/parkinsons_disease/parkinsons_disease.ht m) and UK Brain Bank (http://www.ncbi.nlm.nih.gov/projects/gap/cgi-bin/GetPdf cgi?id=phd000042) at latest follow-up. Patients with secondary parkinsonism at study entry were excluded from this study. Control subjects were recruited from multiple sources, including friends, spouses, and public organizations for elderly and were included in this study if they had provided serum. All patients and controls were Caucasian.

In this study of possible biomarkers for PD we applied a two-stage procedure. For the first discovery phase serum from 16 patients and 8 controls were selected at random. The remaining 164 patients with PD and 182 controls that were eligible for this study were selected for verification purposes. Serum samples were collected at the same day as the clinical examinations and then stored frozen at −70 degrees Celsius until transported to the facilities in New York on dry ice.

Example 1: Analyses of Differentially Expressed Human miRNA by qPCR

RNA Isolation from Serum Samples and QC

After thawing on ice, twenty-four (eight control, sixteen PD samples) serum samples were spun down for 5 mins at 3000×g to remove debris. The supernatant was used to perform small RNA isolation using miRCURY RNA Isolation Kit—Biofluids (Exiqon, MA). Before RNA Isolation, the lysis buffer was spiked with 0.267 fmol/ul of spike-in control cel-miR-39-3p (Qiagen, CA). The remaining part of the RNA isolation was performed following manufacturer's protocol and the isolated RNA was quantified on a Nanodrop 2000 (Thermo Scientific, MA). The RNA was used for running Affymetrix v4 microRNA microarray chips and for subsequent cDNA synthesis and qPCR. RNA from 434 serum samples (22 control and 42 PD from NYPUM study in addition to 190 control and 180 PD from ParkWest project) was isolated as described above, they were not quantified by Nanodrop, but the qPCR data resulting from these samples were normalized by a reference small RNA scaRNA17.

miRNA Microarray and Data Analysis

The isolated RNA from twenty-four patient serum samples were quantified and subjected to Affymetrix GeneChip® miRNA 4.0 Array by the Yale Center for Genome Analysis (http://medicine.yale.edu/keck/ycga/index.aspx). The normalized.CEL files obtained from Affymetrix Expression Console software were imported into Partek Genomics Suite version 6.6 Copyright © 2012 (Partek, MO) for analysis. The 'microRNA Expression Workflow' was employed to detect differentially expressed miRNAs employing ANOVA resulting in lists of miRNAs significantly ($p<0.05$) expressed between control versus PD cohorts. The miRNAs detected were used for further qPCR verification.

Quantitative Polymerase Chain Reaction cDNA for miRNA specific qPCR was synthesized using qScript™ microRNA cDNA Synthesis kit (Quanta Biosciences, MD) following manufacturer's protocol and subsequent qPCRs were performed using miRNAs (Table 1) and PerfeCTa® Universal PCR primer (Quanta Biosciences, MD). scaRNA17 and U6 were used reference small RNAs for normalizing qPCR Cq values whereas cel-miR-39-3p was used as spike-in control. PerfeCTa® SYBR°GREEN SuperMix for IQ™ (Quanta Biosciences, MD) was used for all qPCRs in a MyiQ™ Single color Real-Time PCR Detection System (Bio-Rad, CA). Standard curve for cel-miR-39-3p was analyzed in MS Excel with $R^2=0.97882$ and PCR efficiency 92.96%. No Template Control (NTC) was implied wherever needed.

Data Analysis Based on PD Model

The discriminative ability of miRNAs with regard to PD diagnosis was assessed from ROC analysis using IBM SPSS Statistics, version 21; for combinations of miRNAs the test variable was the predicted probability from logistic regression with PD diagnosis (yes/no) as outcome. To minimize the influence of outlying values on the fit, logistic regression was performed with log transformed miRNA values.

Differentially expressed human miRNAs in Parkinson's disease patients' serum samples from The Norwegian Park-West study were determined employing miRNA microarray. Provided below are the miRNAs with >1.2 fold differential expression.

85 Differentially Expressed Human Pre- and Mature miRNAs with >1.2 Fold Change hsa-miR-548ac, hsa-miR-335-5p, hsa-miR-548x-3p, hsa-miR-520g, hsa-miR-520h, hsa-miR-548ae, hsa-miR-3910-1, hsa-miR-4708-3p, hsa-miR-16-2-3p, hsa-miR-603, hsa-miR-3613-3p, hsa-miR-4797-5p, hsa-miR-548aj-3p, hsa-miR-450b-5p, hsa-miR-548ap-3p, hsa-miR-1184, hsa-miR-2277-5p, hsa-miR-1323, hsa-miR-548aa, hsa-miR-548t-3p, hsa-miR-221-5p, hsa-miR-190a-3p, hsa-miR-6873-5p, hsa-miR-155-3p, hsa-miR-510-5p, hsa-miR-4313, hsa-miR-3616, hsa-miR-8075, hsa-miR-4306, hsa-miR-6776, hsa-miR-6075, hsa-miR-8052, hsa-miR-532, hsa-miR-4791, hsa-miR-320b-1, hsa-miR-548y, hsa-miR-7973, hsa-miR-3136-5p, hsa-miR-606, hsa-miR-500a-3p, hsa-miR-4788, hsa-miR-4769-3p, hsa-miR-299-5p, hsa-miR-4431, hsa-miR-6749-5p, hsa-miR-138-2-3p, hsa-miR-1289-2, hsa-miR-548au, hsa-miR-6850, hsa-miR-561, hsa-miR-34b-5p, hsa-miR-3934-5p, hsa-miR-6739-5p, hsa-miR-4325, hsa-miR-4672, hsa-miR-215-5p, hsa-miR-4685-5p, hsa-miR-3160-1, hsa-miR-3160-2, hsa-miR-6793-5p, hsa-miR-8089, hsa-miR-6081, hsa-miR-892b, hsa-miR-936, hsa-miR-548ag, hsa-miR-345, hsa-miR-548k, hsa-miR-3188, hsa-miR-181b-5p, hsa-let-7e, hsa-miR-4487, hsa-miR-509-3p, hsa-miR-3689a-3p, hsa-miR-4771, hsa-miR-520a-5p, hsa-miR-3150b, hsa-miR-6782-5p, hsa-miR-93'7-5p, hsa-miR-455-3p, hsa-miR-6865-3p, hsa-miR-4749-5p, hsa-miR-378b, hsa-miR-7706, hsa-miR-4445 and hsa-miR-2355-5p.

57 Differentially Expressed Mature miRNAs with >1.2 Fold Change hsa-miR-548ac, hsa-miR-335-5p, hsa-miR-548x-3p, hsa-miR-548ae, hsa-miR-4'708-3p, hsa-miR-16-2-3p, hsa-miR-603, hsa-miR-3613-3p, hsa-miR-4797-5p, hsa-miR-548aj-3p, hsa-miR-450b-5p, hsa-miR-548ap-3p, hsa-miR-1184, hsa-miR-2277-5p, hsa-miR-1323, hsa-miR-548aa, hsa-miR-548t-3p, hsa-miR-221-5p, hsa-miR-190a-3p, hsa-miR-6873-5p, hsa-miR-155-3p, hsa-miR-510-5p, hsa-miR-4313, hsa-miR-4306, hsa-miR-8052, hsa-miR-4791, hsa-miR-7973, hsa-miR-3136-5p, hsa-miR-606, hsa-miR-500a-3p, hsa-miR-4769-3p, hsa-miR-299-5p, hsa-miR-6749-5p, hsa-miR-138-2-3p, hsa-miR-34b-5p, hsa-miR-3934-5p, hsa-miR-6739-5p, hsa-miR-4325, hsa-miR-215-5p, hsa-miR-4685-5p, hsa-miR-6793-5p, hsa-miR-936, hsa-miR-548ag, hsa-miR-548k, hsa-miR-181b-5p, hsa-let-7e, hsa-miR-509-3p, hsa-miR-3689a-3p, hsa-miR-4771, hsa-miR-520a-5p, hsa-miR-6782-5p, hsa-miR-93'7-5p, hsa-miR-455-3p, hsa-miR-6865-3p, hsa-miR-4749-5p, hsa-miR-378b and hsa-miR-2355-5p.

28 Differentially Expressed Premature miRNAs with >1.2 Fold Change hsa-miR-520g, hsa-miR-520h, hsa-miR-3910-1, hsa-miR-3616, hsa-miR-8075, hsa-miR-6776, hsa-miR-6075, hsa-miR-532, hsa-miR-320b-1, hsa-miR-548y, hsa-miR-4788, hsa-miR-4431, hsa-miR-1289-2, hsa-miR-548au, hsa-miR-6850, hsa-miR-561, hsa-miR-4672, hsa-miR-3160-1, hsa-miR-3160-2, hsa-miR-8089, hsa-miR-6081, hsa-miR-892b, hsa-miR-345, hsa-miR-3188, hsa-miR-4487, hsa-miR-3150b, hsa-miR-7706 and hsa-miR-4445.

These differentially expressed miRNA sequences are illustrated below in Table 1, along with the reference/housekeeping small RNAs cel-miR-39-3p, U6 and ScaRNA17 used as controls. Cel-miR-39-3p is a spike-in control that demonstrates the stability of the RNA samples. U6 and ScaRNA17 are used as internal controls to normalize the readings of the rest of the miRNAs or candidate miRNAs.

TABLE 1

| microRNA/small RNA name | microRNA Sequence |
|---|---|
| cel-miR-39-3p | UCACCGGGUGUAAAUCAGCUUG (SEQ ID NO: 1) |
| hsa-let-7e | UGAGGUAGGAGGUUGUAUAGUU (SEQ ID NO: 2) |
| hsa-miR-1184 | CCUGCAGCGACUUGAUGGCUUCC (SEQ ID NO: 3) |
| hsa-miR-1289-2 | CCACGGUCCUAGUUAAAAAGGCACAUUCCUAGACCCUGCCUC AGAACUACUGAACAGAGUCACUGGGUGUGGAGUCCAGGAAUC UGCAUUUUUACCCCUAUCGCCCCCGCC (SEQ ID NO: 4) |
| hsa-miR-1323 | UCAAAACUGAGGGGCAUUUUCU (SEQ ID NO: 5) |
| hsa-miR-138-2-3p | GCUAUUUCACGACACCAGGGUU (SEQ ID NO: 6) |

TABLE 1-continued

| microRNA/small RNA name | microRNA Sequence |
| --- | --- |
| hsa-miR-155-3p | CUCCUACAUAUUAGCAUUAACA (SEQ ID NO: 7) |
| hsa-miR-16-2-3p | CCAAUAUUACUGUGCUGCUUUA (SEQ ID NO: 8) |
| hsa-miR-181b-5p | AACAUUCAUUGCUGUCGGUGGGU (SEQ ID NO: 9) |
| hsa-miR-190a-3p | CUAUAUAUCAAACAUAUUCCU (SEQ ID NO: 10) |
| hsa-miR-215-5p | AUGACCUAUGAAUUGACAGAC (SEQ ID NO: 11) |
| hsa-miR-221-5p | ACCUGGCAUACAAUGUAGAUUU (SEQ ID NO: 12) |
| hsa-miR-2277-5p | AGCGCGGGCUGAGCGCUGCCAGUC (SEQ ID NO: 13) |
| hsa-miR-2355-5p | AUCCCCAGAUACAAUGGACAA (SEQ ID NO: 14) |
| hsa-miR-299-5p | UGGUUUACCGUCCCACAUACAU (SEQ ID NO: 15) |
| hsa-miR-3136-5p | CUGACUGAAUAGGUAGGGUCAUU (SEQ ID NO: 16) |
| hsa-miR-3150b | GAGGGAAAGCAGGCCAACCUCGAGGAUCUCCCCAGCCUUGGC GUUCAGGUGCUGAGGAGAUCGUCGAGGUUGGCCUGCUUCCCC UC (SEQ ID NO: 17) |
| hsa-miR-3160-1 | GGACCUGCCCUGGGCUUUCUAGUCUCAGCUCUCCUCCAGCUC AGCUGGUCAGGAGAGCUGAGACUAGAAAGCCCAGGGCAGGUUC (SEQ ID NO: 18) |
| hsa-miR-3160-2 | ACCUGCCCUGGGCUUUCUAGUCUCAGCUCUCCUGACCAGCUG AGCUGGAGGAGAGCUGAGACUAGAAAGCCCAGGGCAGGU (SEQ ID NO: 19) |
| hsa-miR-3188 | GGCGCCUCCUGCUCUGCUGUGCCGCCAGGGCCUCCCCUAGCGC GCCUUCUGGAGAGGCUUUGUGCGGAUACGGGGCUGGAGGCCU (SEQ ID NO: 20) |
| hsa-miR-320b-1 | AAUUAAUCCCUCUCUUUCUAGUUCUUCCUAGAGUGAGGAAAA GCUGGGUUGAGAGGGCAAACAAAUUAACUAAUUAAUU (SEQ ID NO: 21) |
| hsa-miR-335-5p | UCAAGAGCAAUAACGAAAAAUGU (SEQ ID NO: 22) |
| hsa-miR-345 | ACCCAAACCCUAGGUCUGCUGACUCCUAGUCCAGGGCUCGUG AUGGCUGGUGGGCCCUGAACGAGGGGUCUGGAGGCCUGGGUU UGAAUAUCGACAGC (SEQ ID NO: 23) |
| hsa-miR-34b-5p | UAGGCAGUGUCAUUAGCUGAUUG (SEQ ID NO: 24) |
| hsa-miR-3613-3p | ACAAAAAAAAAAGCCCAACCCUUC (SEQ ID NO: 25) |
| hsa-miR-3616 | UGUCACUCCGCCAGCAUCAUGAAGUGCACUCAUGAUAUGUUU GCCCCAUCAGCGUGUCACGAGGGCAUUUCAUGAUGCAGGCGG GGUUGGCA (SEQ ID NO: 26) |
| hsa-miR-3689a-3p | CUGGGAGGUGUGAUAUCGUGGU (SEQ ID NO: 27) |
| hsa-miR-378b | ACUGGACUUGGAGGCAGAA (SEQ ID NO: 28) |
| hsa-miR-3910-1 | CUUUUGCUGUCAGUUUUUCUGUUGCUUGUCUUGGUUUUAUGC CUUUUAUAUCAAGGCACAUAAAAGGCAUAAAACCAAGACAAG CAACAAAAAAAGGAUUGAUCACAGAAG (SEQ ID NO: 29) |
| hsa-miR-3934-5p | UCAGGUGUGGAAACUGAGGCAG (SEQ ID NO: 30) |
| hsa-miR-4306 | UGGAGAGAAAGGCAGUA (SEQ ID NO: 31) |
| hsa-miR-4313 | AGCCCCCUGGCCCCAAACCC (SEQ ID NO: 32) |
| hsa-miR-4325 | UUGCACUUGUCUCAGUGA ( SEQ ID NO: 33) |
| hsa-miR-4431 | UGGUUUGCGACUCUGAAAACUAGAAGGUUUAUGACUGGGCA UUUCUCACCCAAUGCCCAAUAUUGAACUUUCUAGUUGUCAGA GUCAUUAACCC (SEQ ID NO: 34) |
| hsa-miR-4445 | UUCCUGCAGAUUGUUUCUUUUGCCGUGCAAGUUUAAGUUUUU GCACGGCAAAAGAAACAAUCCAGAGGGU ( SEQ ID NO: 35) |

TABLE 1-continued

| microRNA/small RNA name | microRNA Sequence |
|---|---|
| hsa-miR-4487 | ACUGUCCUUCAGCCAGAGCUGGCUGAAGGGCAGAAGGGAACU GUCCUUCAGCCAGAGCUGGCUGAAGGGCAGA (SEQ ID NO: 36) |
| hsa-miR-450b-5p | UUUUGCAAUAUGUUCCUGAAUA (SEQ ID NO: 37) |
| hsa-miR-455-3p | GCAGUCCAUGGGCAUAUACAC (SEQ ID NO: 38) |
| hsa-miR-4672 | GGCUGCUUCUCGCCUCUGUCCAGCUGUGUGGCCUUGGACAAG CCUCUUGGUUACACAGCUGGACAGAGGCACGAAACAGCC (SEQ ID NO: 39) |
| hsa-miR-4685-5p | CCCAGGGCUUGGAGUGGGGCAAGGUU (SEQ ID NO: 40) |
| hsa-miR-4708-3p | AGCAAGGCGGCAUCUCUCUGAU (SEQ ID NO: 41) |
| hsa-miR-4749-5p | UGCGGGACAGGCCAGGGCAUC (SEQ ID NO: 42) |
| hsa-miR-4769-3p | UCUGCCAUCCUCCCUCCCCUAC (SEQ ID NO: 43) |
| hsa-miR-4771 | AGCAGACUUGACCUACAAUUA (SEQ ID NO: 44) |
| hsa-miR-4788 | AAUGAAGGAUUACGGACCAGCUAAGGGAGGCAUUAGGAUCCU UAUUCUUGCCUCCCUUAGUUGGUCCCUAAUCCUUCGUU (SEQ ID NO: 45) |
| hsa-miR-4791 | UGGAUAUGAUGACUGAAA (SEQ ID NO: 46) |
| hsa-miR-4797-5p | GACAGAGUGCCACUUACUGAA (SEQ ID NO: 47) |
| hsa-miR-500a-3p | AUGCACCUGGGCAAGGAUUCUG (SEQ ID NO: 48) |
| hsa-miR-509-3p | UGAUUGGUACGUCUGUGGGUAG (SEQ ID NO: 49) |
| hsa-miR-510-5p | UACUCAGGAGAGUGGCAAUCAC (SEQ ID NO: 50) |
| hsa-miR-520a-5p | CUCCAGAGGGAAGUACUUUCU (SEQ ID NO: 51) |
| hsa-miR-520g | UCCCAUGCUGUGACCCUCUAGAGGAAGCACUUUCUGUUUGUU GUCUGAGAAAAACAAAGUGCUUCCCUUUAGAGUGUUACCGU UUGGGA (SEQ ID NO: 52) |
| hsa-miR-520h | UCCCAUGCUGUGACCCUCUAGAGGAAGCACUUUCUGUUUGUU GUCUGAGAAAAACAAAGUGCUUCCCUUUAGAGUUACUGUUU GGGA (SEQ ID NO: 53) |
| hsa-miR-532 | CGACUUGCUUUCUCUCCUCCAUGCCUUGAGUGUAGGACCGUU GGCAUCUUAAUUACCCUCCCACACCCAAGGCUUGCAGAAGAG CGAGCCU (SEQ ID NO: 54) |
| hsa-miR-548aa | AAAAACCACAAUUACUUUUGCACCA (SEQ ID NO: 55) |
| hsa-miR-548ac | CAAAAACCGGCAAUUACUUUUG (SEQ ID NO: 56) |
| hsa-miR-548ae | CAAAAACUGCAAUUACUUUCA (SEQ ID NO: 57) |
| hsa-miR-548ag | AAAGGUAAUUGUGGUUUCUGC (SEQ ID NO: 58) |
| hsa-miR-548aj-3p | UAAAAACUGCAAUUACUUUUA ( SEQ ID NO: 59) |
| hsa-miR-548ap-3p | AAAAACCACAAUUACUUUU (SEQ ID NO:60) |
| hsa-miR-548au | AAAAGUAAUUGCGGUUUUUGCUAUUGGUUUUAAUGGCAGUU ACUUUUGCACCAG (SEQ ID NO: 61) |
| hsa-miR-548k | AAAGUACUUGCGGAUUUUGCU (SEQ ID NO: 62) |
| hsa-miR-548t-3p | AAAAACCACAAUUACUUUUGCACCA (SEQ ID NO: 63) |
| hsa-miR-548x-3p | UAAAAACUGCAAUUACUUUC (SEQ ID NO: 64) |
| hsa-miR-548y | GCCUAAACUAUUAGGUUGGUGCAAAAGUAAUCACUGUUUUU GCCAUUACUCUCAGUGGCAAAAACCGUGAUUACUUUUGCACC AACCUAGUAAACACCUUCACUGUGGGGG (SEQ ID NO: 65) |

TABLE 1-continued

| microRNA/small RNA name | microRNA Sequence |
|---|---|
| hsa-miR-561 | CUUCAUCCACCAGUCCUCCAGGAACAUCAAGGAUCUUAAACU UUGCCAGAGCUACAAAGGCAAAGUUUAAGAUCCUUGAAGUUC CUGGGGGAACCAU (SEQ ID NO: 66) |
| hsa-miR-603 | CACACACUGCAAUUACUUUUGC (SEQ ID NO: 67) |
| hsa-miR-606 | AAACUACUGAAAAUCAAAGAU (SEQ ID NO: 68) |
| hsa-miR-6075 | GACACCACAUGCUCCUCCAGGCCUGCCUGCCCUCCAGGUCAU GUUCCAGUGUCCCACAGAUGCAGCACCACGGCCCAGGCGGCA UUGGUGUCACC (SEQ ID NO: 69) |
| hsa-miR-6081 | CCACCACGGUGCUGGCACCAGGGCCUCUGCCCCGUAGGACAC CGAGGCUUUAUGAAUAGGAGCAGUGCCGGCCAAGGCGCCGGCA CCAUCUUGGUGAU (SEQ ID NO: 70) |
| hsa-miR-6739-5p | UGGGAAAGAGAAAGAACAAGUA (SEQ ID NO: 71) |
| hsa-miR-6749-5p | UCGGGCCUGGGGUUGGGGGAGC (SEQ ID NO: 72) |
| hsa-miR-6776 | CGGGCUCUGGGUGCAGUGGGGGUUCCCACGCCGCGGCAACCA CCACUGUCUCUCCCCAG (SEQ ID NO: 73) |
| hsa-miR-6782-5p | UAGGGGUGGGGGAAUUCAGGGGUGU (SEQ ID NO: 74) |
| hsa-miR-6793-5p | UCCCCAACCCCUGCCCGCAG (SEQ ID NO: 75) |
| hsa-miR-6850 | GUGCGGAACGCUGGCCGGGGCGGGAGGGGAAGGGACGCCCGG CCGGAACGCCGCACUCACG (SEQ ID NO: 76) |
| hsa-miR-6865-3p | ACACCCUCUUUCCCUACCGCC (SEQ ID NO: 77) |
| hsa-miR-6873-5p | CAGAGGGAAUACAGAGGGCAAU (SEQ ID NO: 78) |
| hsa-miR-7706 | UGGAGCUGUGUGCAGGGCCAGCGCGGAGCCCGAGCAGCCGCG GUGAAGCGCCUGUGCUCUGCCGAGA (SEQ ID NO: 79) |
| hsa-miR-7973 | UGUGACCCUAGAAUAAUUAC (SEQ ID NO: 80) |
| hsa-miR-8052 | CGGGACUGUAGAGGGCAUGAGC (SEQ ID NO: 81) |
| hsa-miR-8075 | CCUUGCUGAUGGCAGAUGUCGGAUCUGCCUCGCUUAUACGUG CCCUUGCUGAUGCAGAUGUCGGGUCUGCCUCGCUUAU (SEQ ID NO: 82) |
| hsa-miR-8089 | AAGGAGCACUCACUCCAAUUUCCCUGGACUGGGGGCAGGCUG CCACCUCCUGGGGACAGGGGAUUGGGGCAGGAUGUUCCAG (SEQ ID NO: 83) |
| hsa-miR-892b | UGCAAUGCCCUACUCAGAAAGGUGCCAUUUAUGUAGAUUUUA UGUCACUGGCUCCUUUCUGGGUAGAGCAAGGCUCA (SEQ ID NO: 84) |
| hsa-miR-936 | ACAGUAGAGGGAGGAAUCGCAG (SEQ ID NO: 85) |
| hsa-miR-937-5p | GUGAGUCAGGGUGGGGCUGG (SEQ ID NO: 86) |
| scaRNA17 | AGAGGCUUGGGCCGCCGAGCUGGACCCGGACCGGUUUUGGGU ACUGUACUGGGGCAGGGCAGAGAGGG (SEQ ID NO: 87) |
| U6 | GUGCUCGCULCGGCAGCACAUAUACUAAAAUUGGAACGAUAC AGAGAAGAUUAGCAUGGCCCCUGCGCAAGGAUGACACGCAAA UUCGUGAAGCGUUCCAUAUUUU (SEQ ID NO: 88) |

Example 2: Verification of Human Mature miRNAs by qPCR in Sample Cohort of 16 Patients and 8 Controls The mean fold change for hsa-miR-335-5p, hsa-miR-3613-3p and hsa-miR-6865-3p PARKmiRs between PD patients and healthy controls are shown below in Table 2 and illustrated in FIG. 1.

TABLE 2

| PARKmiR | Fold change | Significance |
|---|---|---|
| hsa-miR-335-5p | 1.64 | 0.02 |
| hsa-miR-3613-3p | 2.16 | 0.004 |
| hsa-miR-6865-3p | 1.65 | 0.03 |

Example 3: Analyses of Hsa-miR-335-5p and Hsa-miR-6865-3p in a Cohort of 346 Individuals (182 Control and 164 PD Serum Samples) from Norwegian ParkWest Study The qPCR technique of Example 2 was used to identify potential diagnostic biomarkers. It was determined that combinations of hsa-miR-335-5p and hsa-miR-6865-3p show high predictability for PD diagnosis. The results of the model with hsa-miR-335-5p and hsa-miR-6865-3p, Outcome=PD (YES/NO), n=164 cases+182 controls are shown below in Table 3.

TABLE 3

Statistical analysis of individual and combination of PARKmiRs from 164 PD patients and 182 controls

| miRNA(s) | Patients (n = 164) median (IQR) | Controls (n = 182) median (IQR) | p¹ | AUC (95% CI) | p² |
|---|---|---|---|---|---|
| 335 | 1.4 (0.5 to 2.7) | 0.12 (0.06 to 0.22) | <0.001 | 0.90 (0.87 to 0.93) | <0.001 |
| 6865 | 2.7 (1.1 to 6.9) | 1.0 (0.8 to 1.5) | <0.001 | 0.74 (0.69 to 0.80) | <0.001 |
| 3613 | 0.41 (0.19 to 0.92) | 0.21 (0.09 to 0.49) | <0.001 | 0.65 (0.59 to 0.71) | <0.001 |
| 335/6865 | | | | 0.90 (0.87 to 0.93) | <0.001 |
| 335/3613 | | | | 0.90 (0.87 to 0.94) | <0.001 |

Figure 2A:
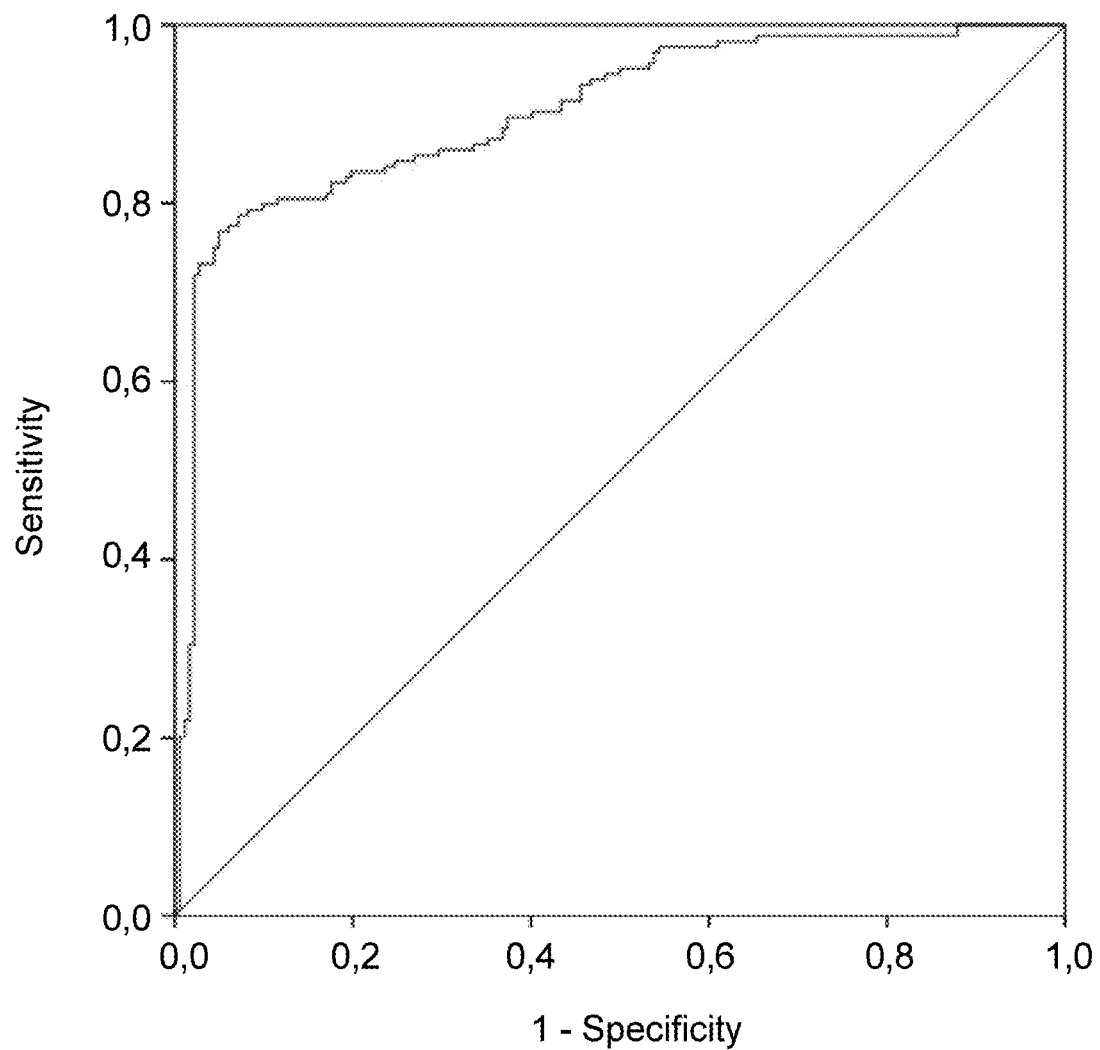
FIG. 2A is a ROC analysis based on predicted probabilities from the model and compared to true disease status.

ROC analysis based on predicted probabilities compared to true disease status is depicted in FIG. 2a, and show strong discriminating ability. The area under the curve of FIG. 2a is provided in Table 3 above.

Example 4: Analyses of Hsa-miR-335-5p and Hsa-miR-3613-3p in a Cohort of 346 Individuals (182 Control and 164 PD Serum Samples)

Following the protocol of Example 3 it was determined that combinations of hsa-miR-335-5p and hsa-miR-3613-3p also show high predictability for PD diagnosis. The results of the model with hsa-miR-335-5p and hsa-miR-3613-3p, Outcome=PD (YES/NO), n=164 cases+182 controls are shown above in Table 3.

Figure 2B:
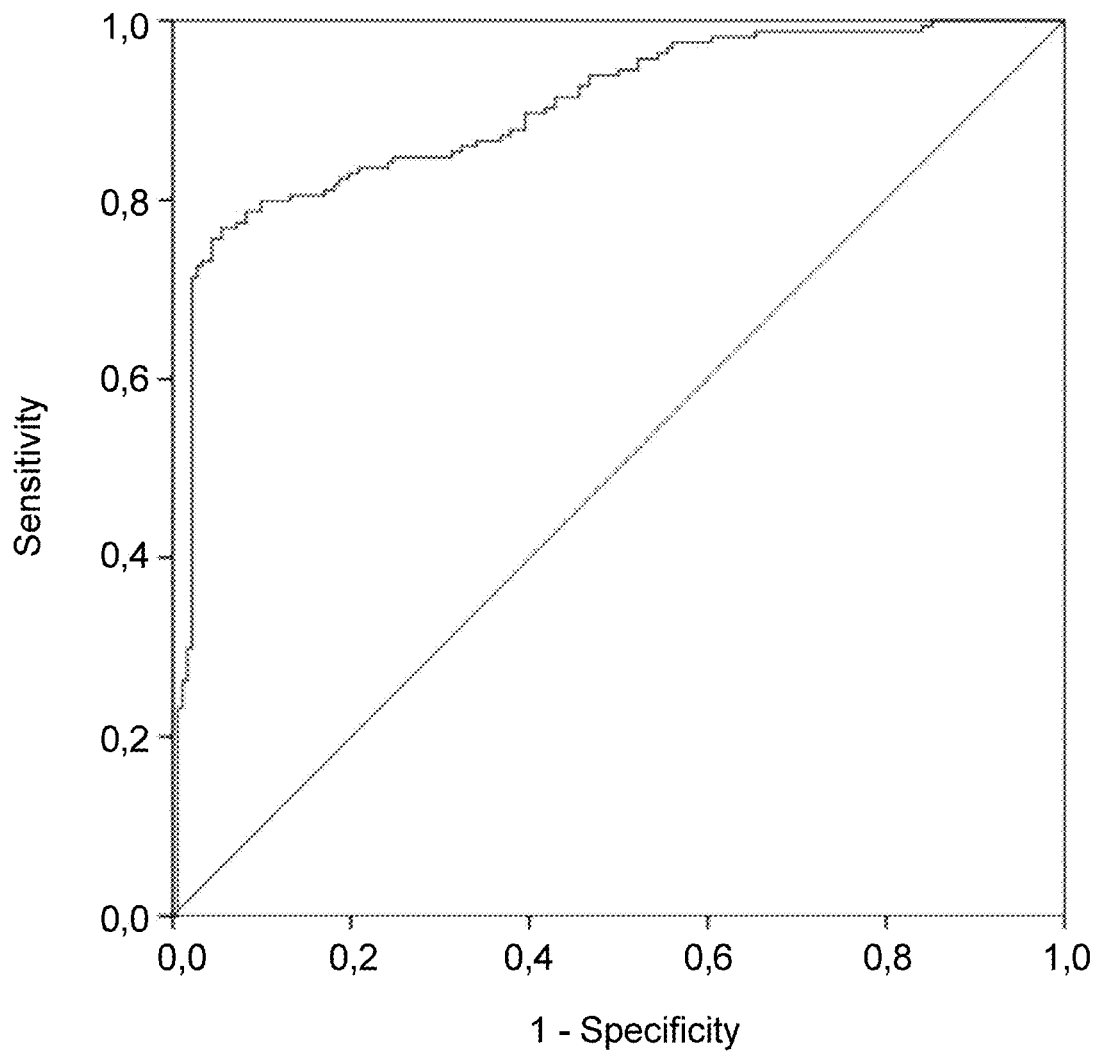
FIG. 2B is a ROC analysis based on predicted prohibition from the model.

ROC analysis based on predicted probabilities from the model showing strong discriminating ability are depicted in FIG. 2b. The area under the curve of FIG. 2b is provided in Table 3 above.

From the foregoing Examples 1-4 it is evidenced that any combination of two or more microRNAs from the list of 85 identified miRNAs can be used to diagnose the occurrence of PD in patients.

Example 5: hsa-miR-335-5p

Table 3 above illustrates that hsa-miR-335-5p shows high predictability for PD diagnosis for Outcome=PD (YES/NO), n=164 cases+182 controls.

Figure 3:
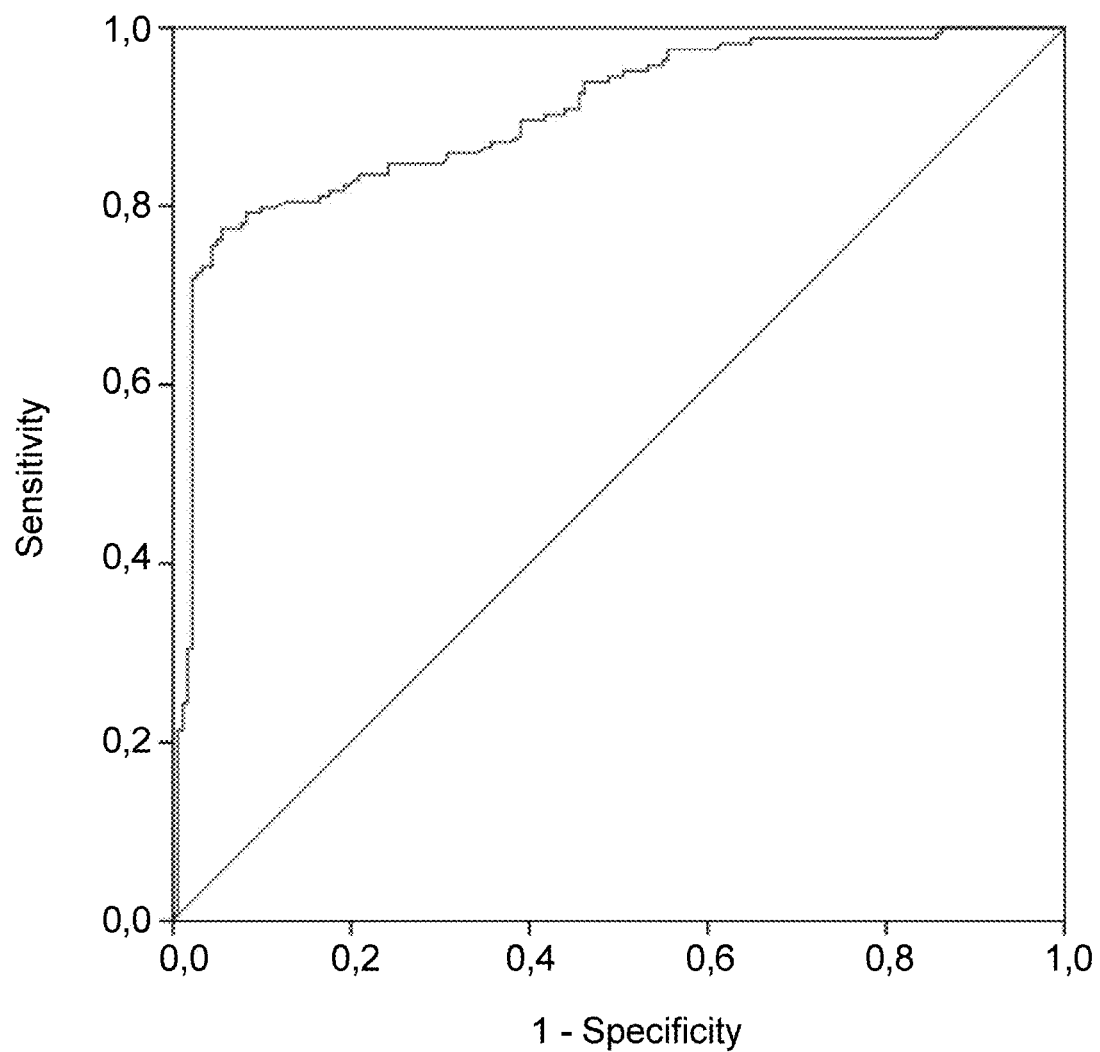
FIG. 3 is a ROC analysis based on predicted probabilities from the model and compared to true disease status.

ROC analysis based on probabilities from the model and compared to true disease status showing strong discriminating ability is shown in FIG. 3. The area under the curve of FIG. 3 is provided in Table 3 above.

Figure 4:
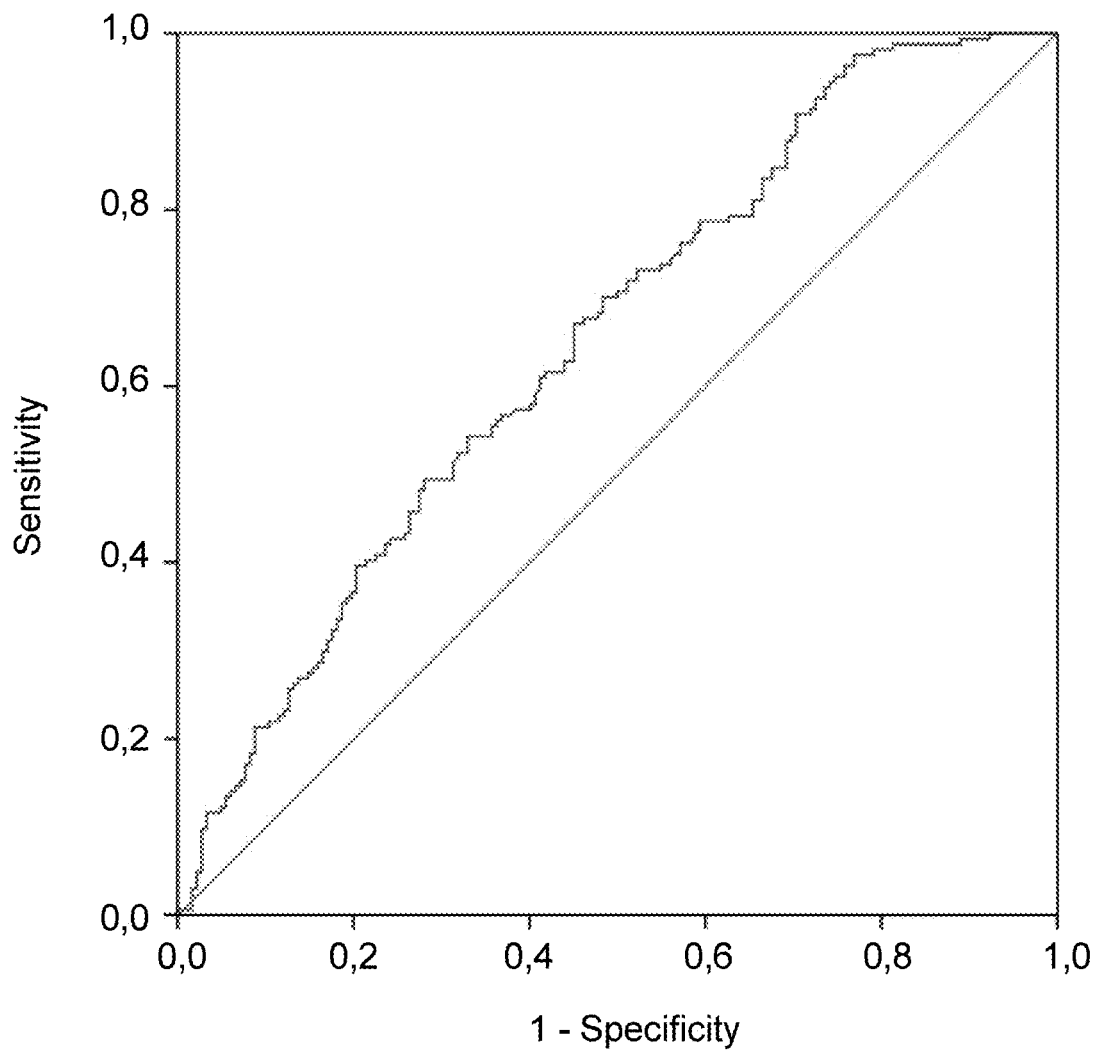
FIG. 4 is a ROC analysis based on predicted probabilities from the model and compared to true disease status.

Example 6: has-miR-3613-3p hsa-miR-3613-3p also shows high predictability for PD diagnosis as illustrated in Table 3 above. ROC analysis based on probabilities from the model and compared to true disease status showing strong discriminating ability is shown in FIG. 4. The area under the curve of FIG. 4 is provided in Table 3 above.

Example 7: has-miR-6865-3p

Figure 5:
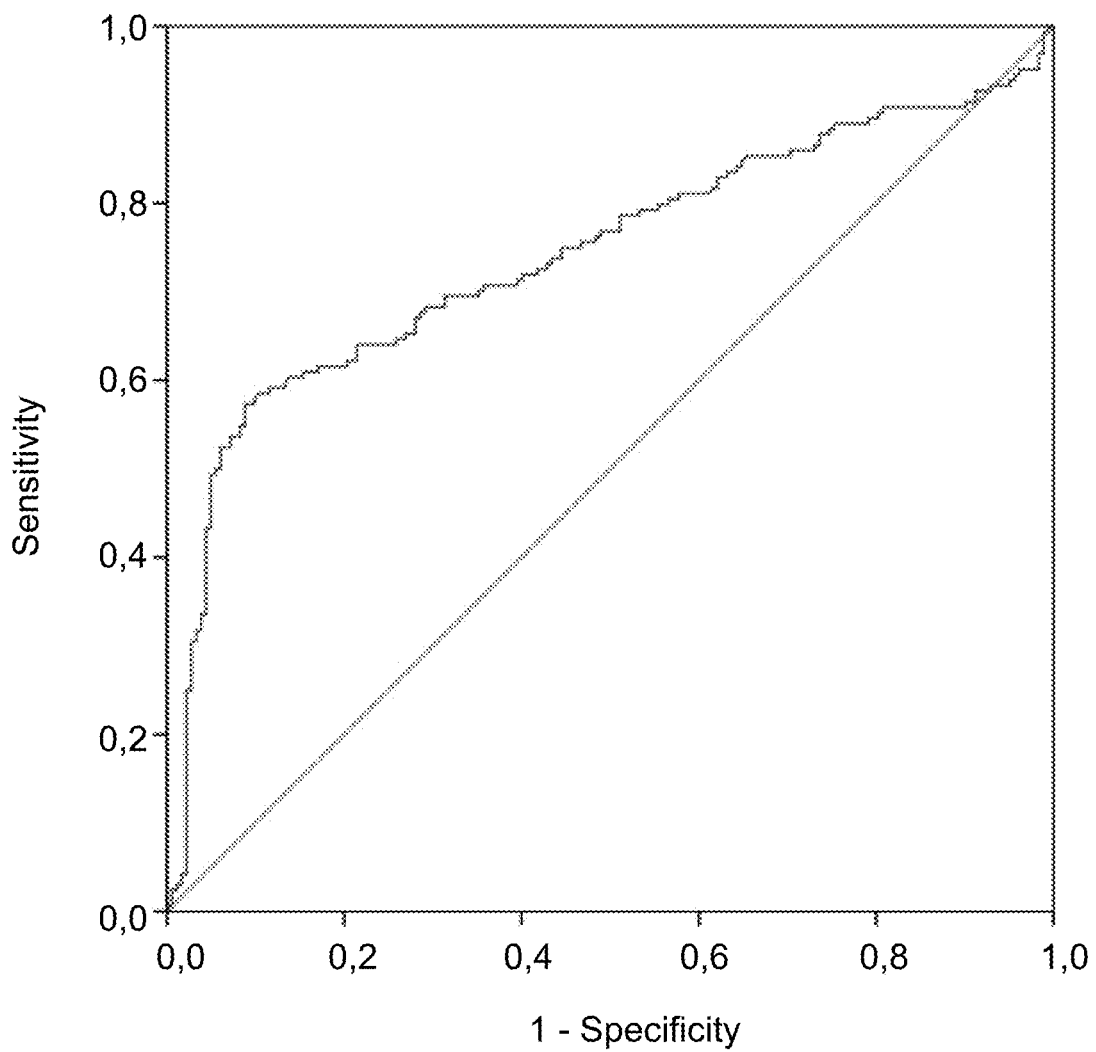
FIG. 5 is a ROC analysis based on predicted probabilities from the model and compared to true disease status.

Similarly, hsa-miR-6865-3p also shows high predictability for PD diagnosis as shown in Table 3 above. ROC analysis based on probabilities from the model and compared to true disease status showing strong discriminating ability is shown in FIG. 5. The area under the curve of FIG. 5 is provided above in Table 3.

From the foregoing Examples 5-7, it is evidenced that hsa-miR-335-5p, hsa-miR-3613-3p and hsa-miR-6865-3p may be used individually for accurate diagnosis of PD.

Example 8: Analyses of hsa-miR-335-5p and hsa-miR-6865-3p in a Cohort of 64 Individuals (22 Control and 42 PD Serum Samples) from Swedish NYPUM Study The qPCR technique of Example 2 was used to validate the diagnostic biomarkers of Example 2. It was determined that combinations of hsa-miR-335-5p and hsa-miR-6865-3p show high predictability for PD diagnosis. The results of the model with hsa-miR-335-5p and hsa-miR-6865-3p, Outcome=PD (YES/NO), n=42 cases+22 controls are shown below in Table 4.

TABLE 4

Statistical analysis of individual and combinations of PARKmiRs from 42 PD patients and 22 controls from the NYPUM study.

| miRNA(s) | Patients (n = 42) median (IQR) | Controls (n = 22) median (IQR) | p¹ | AUC (95% CI) | p² |
|---|---|---|---|---|---|
| 335 | 1.3 (0.79 to 2.2) | 1.1 (0.71 to 1.4) | 0.125 | 0.62 (0.48 to 0.75) | 0.127 |
| 3613 | 2.1 (1.2 to 3.3) | 1.2 (1.0 to 1.6) | 0.012 | 0.74 (0.62 to 0.86) | 0.002 |
| 6865 | 1.5 (1.2 to 2.2) | 1.2 (1.0 to 1.4) | 0.002 | 0.69 (0.56 to 0.82) | 0.012 |
| 335/3613 | n/a | n/a | n/a | 0.75 (0.63 to 0.87) | 0.001 |
| 335/6865 | n/a | n/a | n/a | 0.71 (0.59 to 0.84) | 0.006 |
| 3613/6865 | n/a | n/a | n/a | 0.75 (0.63 to 0.87) | 0.001 |
| 335/3613/6865 | n/a | n/a | n/a | 0.76 (0.64 to 0.87) | 0.001 |

Figure 7:
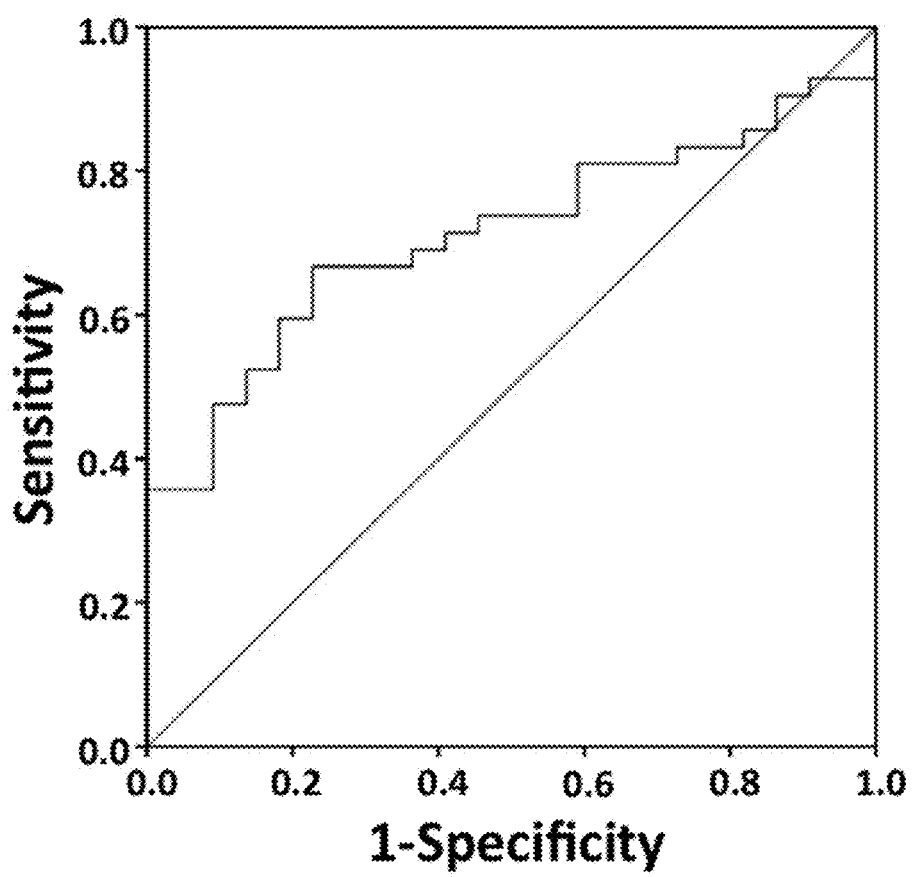
FIG. 7 is a ROC analysis based on predicted probabilities from the model and compared to true disease status.

ROC analysis based on predicted probabilities compared to true disease status is depicted in FIG. 7, and show strong discriminating ability. The area under the curve of FIG. 7 is provided in Table 4 above.

Example 9: Analyses of Hsa-miR-335-5p and Hsa-miR-3613-3p in a Cohort of 64 Individuals (22 Control and 42 PD Serum Samples)

Following the protocol of Example 3 it was determined that combinations of hsa-miR-335-5p and hsa-miR-3613-3p also show high predictability for PD diagnosis. The results of the model with hsa-miR-335-5p and hsa-miR-3613-3p, Outcome=PD (YES/NO), n=42 cases+22 controls are shown above in Table 4.

Figure 8:
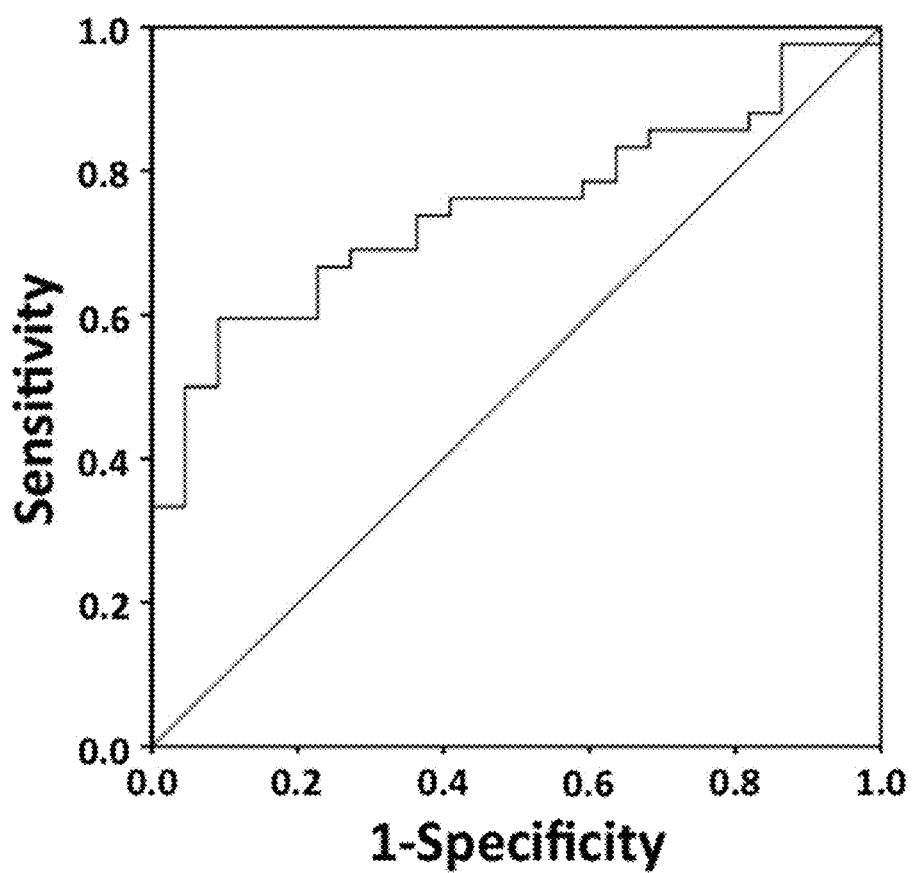
FIG. 8 is a ROC analysis based on predicted probabilities from the model and compared to true disease status.

ROC analysis based on predicted probabilities from the model showing strong discriminating ability are depicted in FIG. 8. The area under the curve of FIG. 8 is provided in Table 4 above.

Example 10: Analyses of Hsa-miR-3613-3p and Hsa-miR-6865-5p in a Cohort of 64 Individuals (22 Control and 42 PD Serum Samples)

Following the protocol of Example 3 it was determined that combinations of hsa-miR-3613-3p and hsa-miR-6865-5p also show high predictability for PD diagnosis. The results of the model with hsa-miR-3613-3p and hsa-miR-6865-5p, Outcome=PD (YES/NO), n=42 cases+22 controls are shown above in Table 4.

Figure 9:
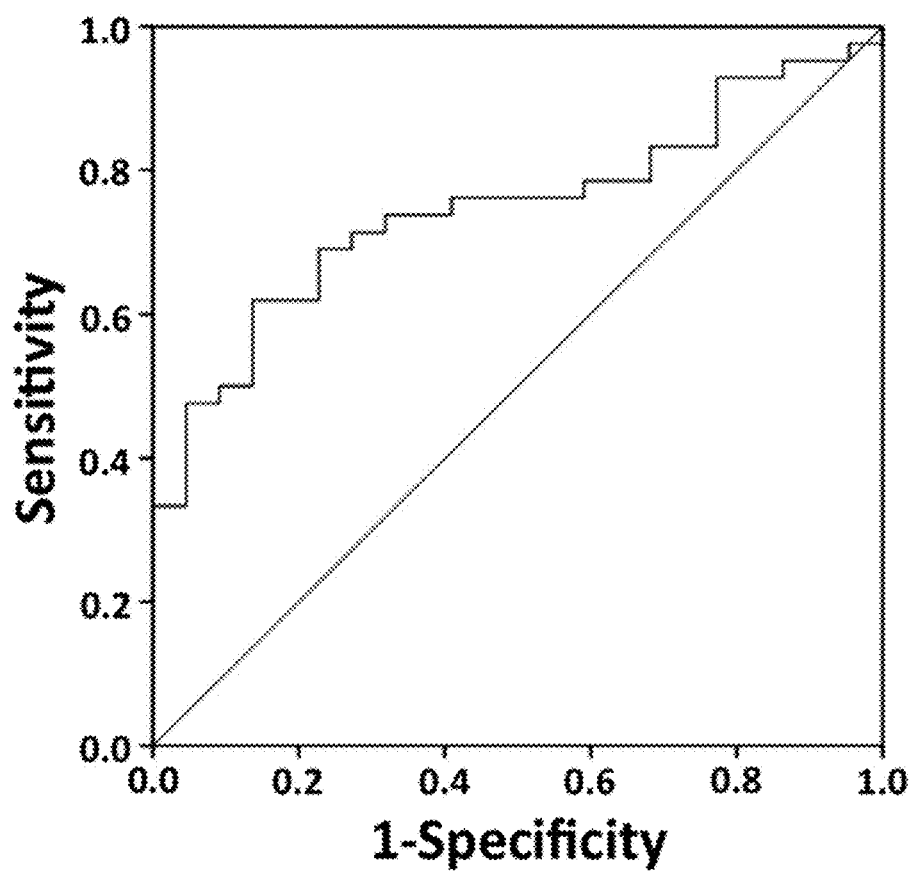
FIG. 9 is a ROC analysis based on predicted probabilities from the model and compared to true disease status.

ROC analysis based on predicted probabilities from the model showing strong discriminating ability are depicted in FIG. 9. The area under the curve of FIG. 9 is provided in Table 4 above.

Example 11: Analyses of Hsa-miR-335-5p, Hsa-miR-3613-3p and Hsa-miR-6865-5p in a Cohort of 64 Individuals (22 Control and 42 PD Serum Samples)

Following the protocol of Example 3 it was determined that combinations of hsa-miR-hsa-miR-335-5p, hsa-miR-3613-3p and hsa-miR-6865-5p also show high predictability for PD diagnosis. The results of the model with hsa-miR-335-5p, hsa-miR-3613-3p and hsa-miR-6865-5p, Outcome=PD (YES/NO), n=42 cases+22 controls are shown above in Table 4.

Figure 10:
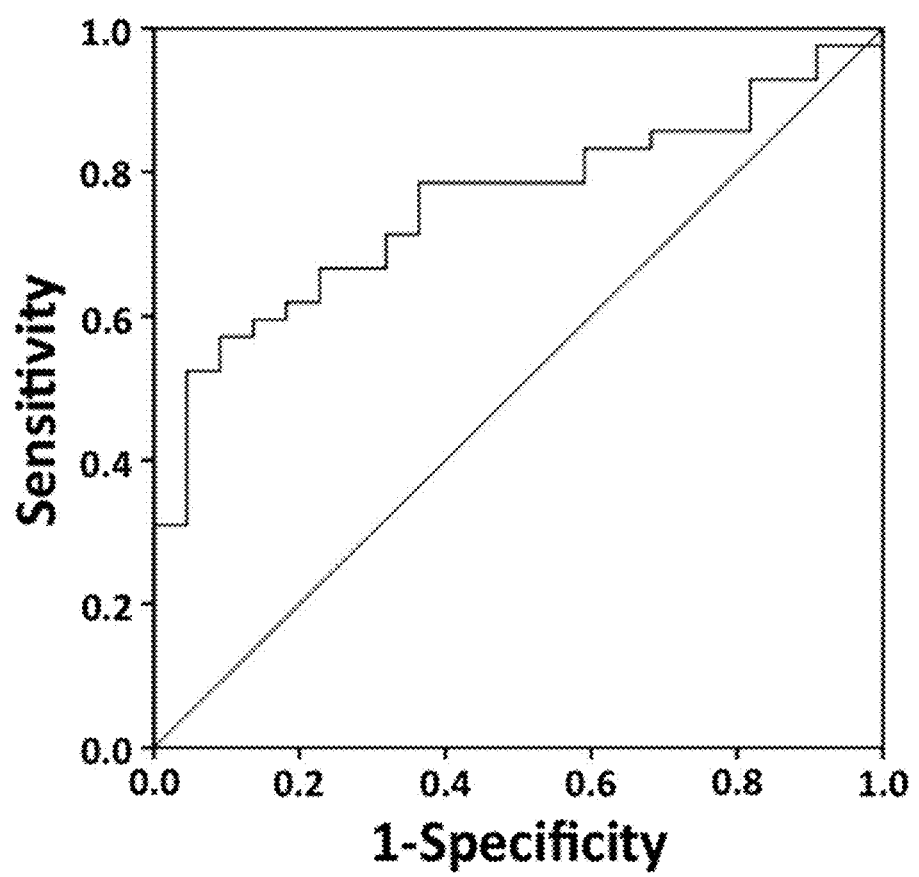
FIG. 10 is a ROC analysis based on predicted probabilities from the model and compared to true disease status.

ROC analysis based on predicted probabilities from the model showing strong discriminating ability are depicted in FIG. 10. The area under the curve of FIG. 10 is provided in Table 4 above.

From the foregoing Example 10 it is evidenced that any combination of three or more microRNAs from the list of 85 identified miRNAs can be used to diagnose the occurrence of PD in patients.

Example 12

Figure 6A:
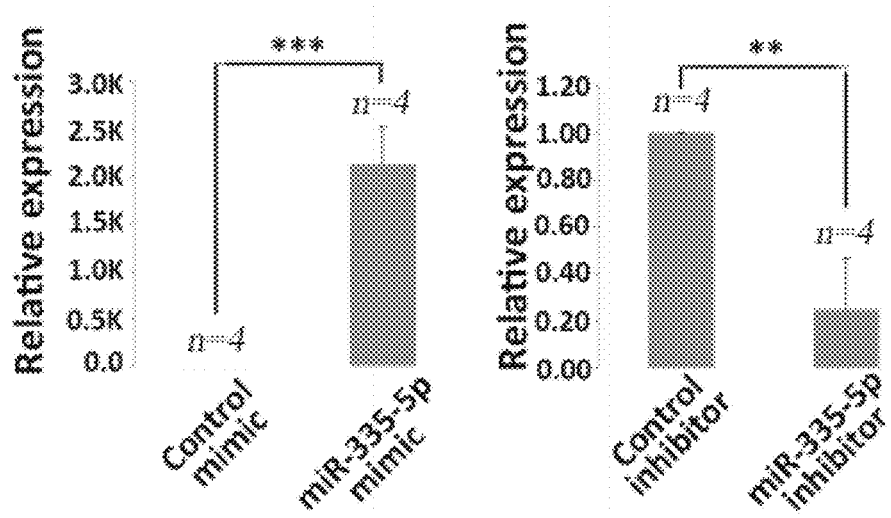
FIG. 6(A)-(H) illustrate microRNAs targeting Parkinson's Disease proteins.
Figure 6B:
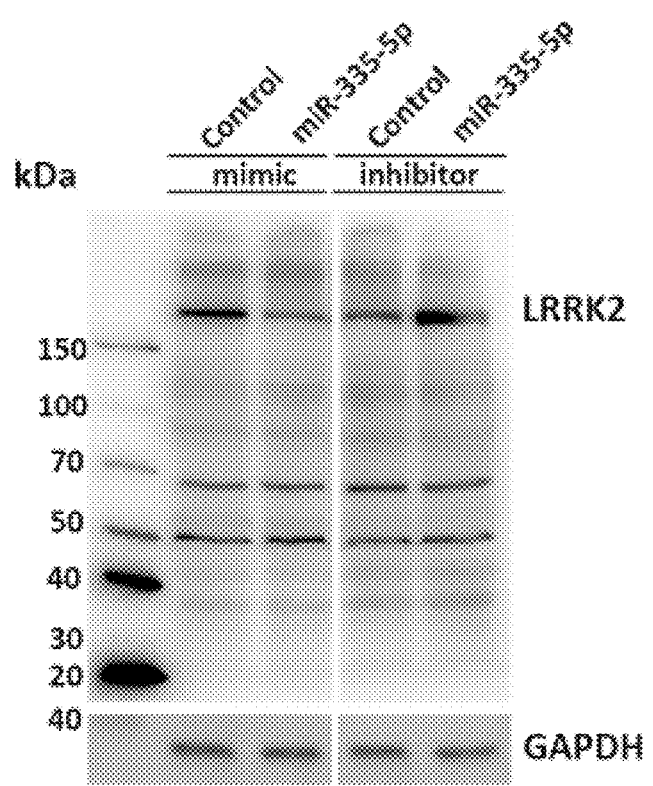
Figure 6C:
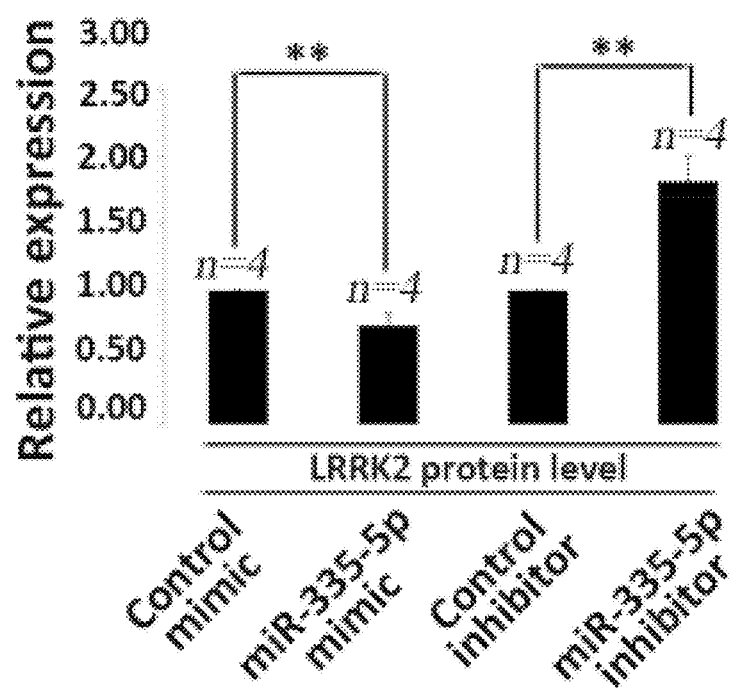
Figure 6D:
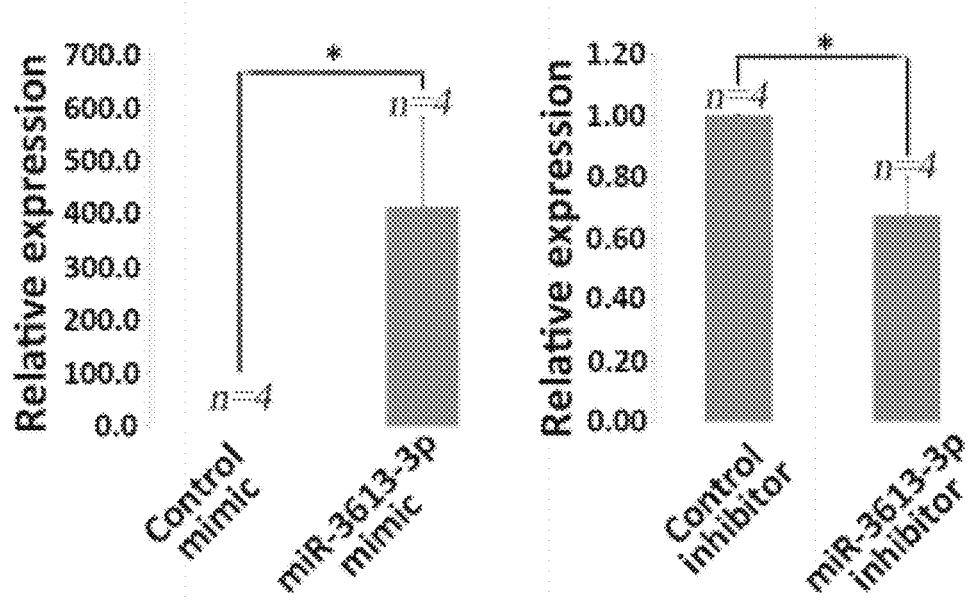
Figure 6E:
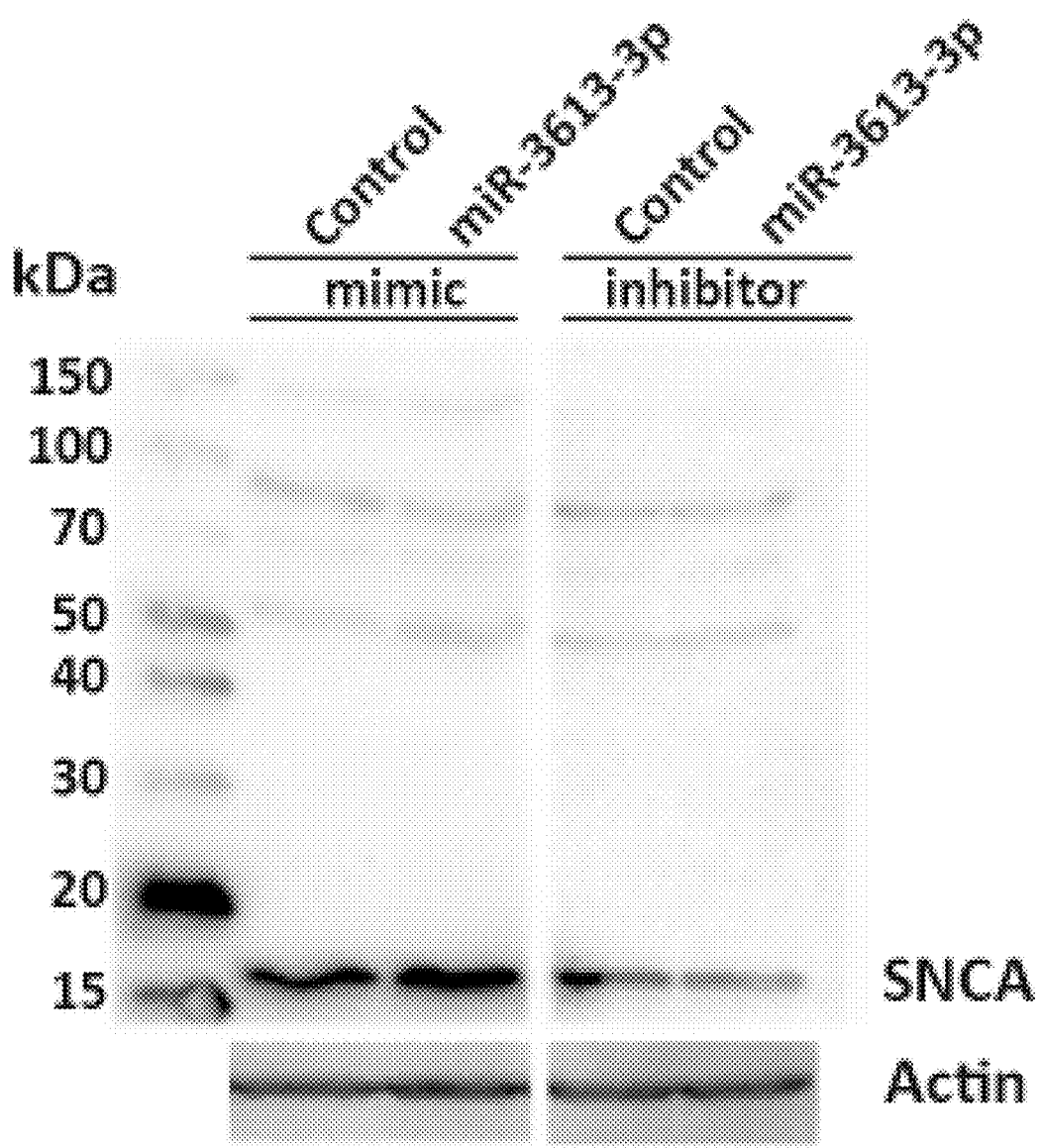
Figure 6F:
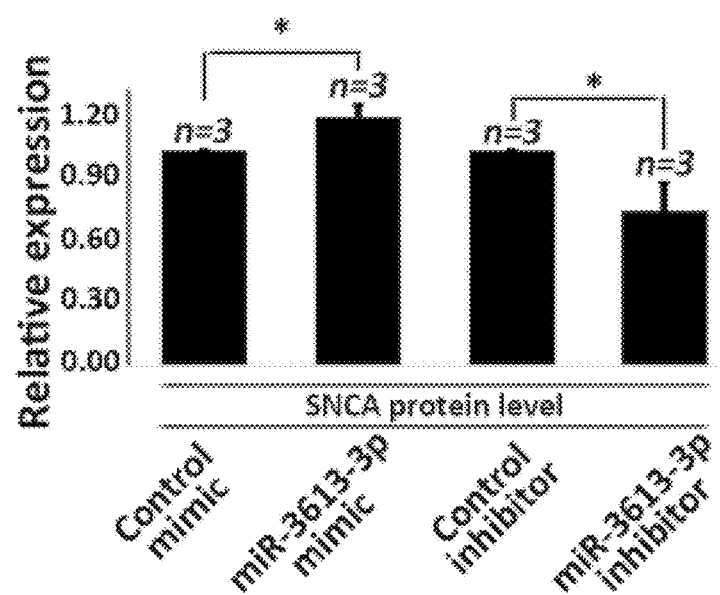
Figure 6G:
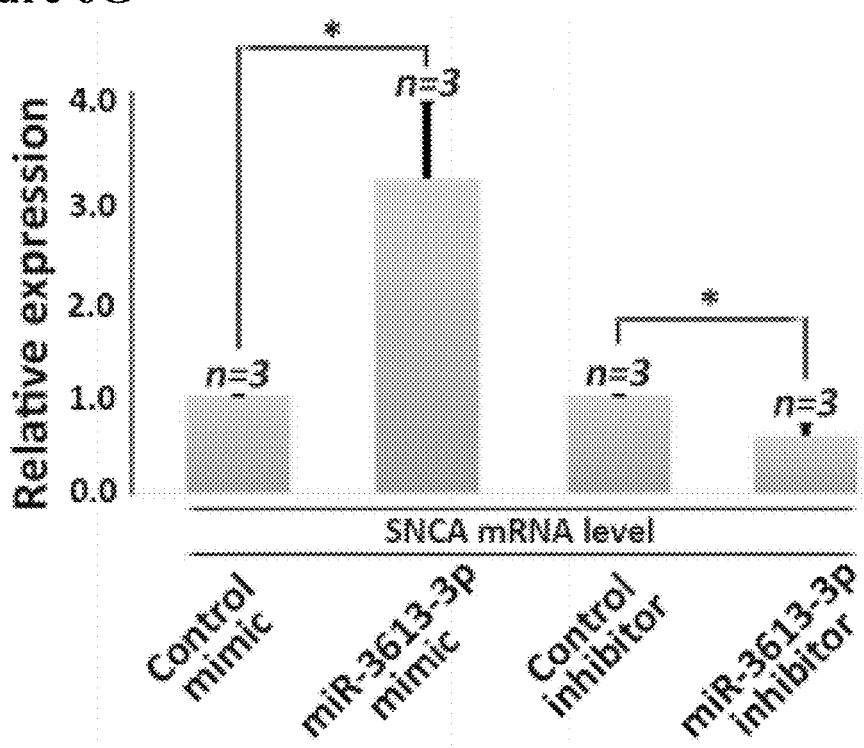
Figure 6H:
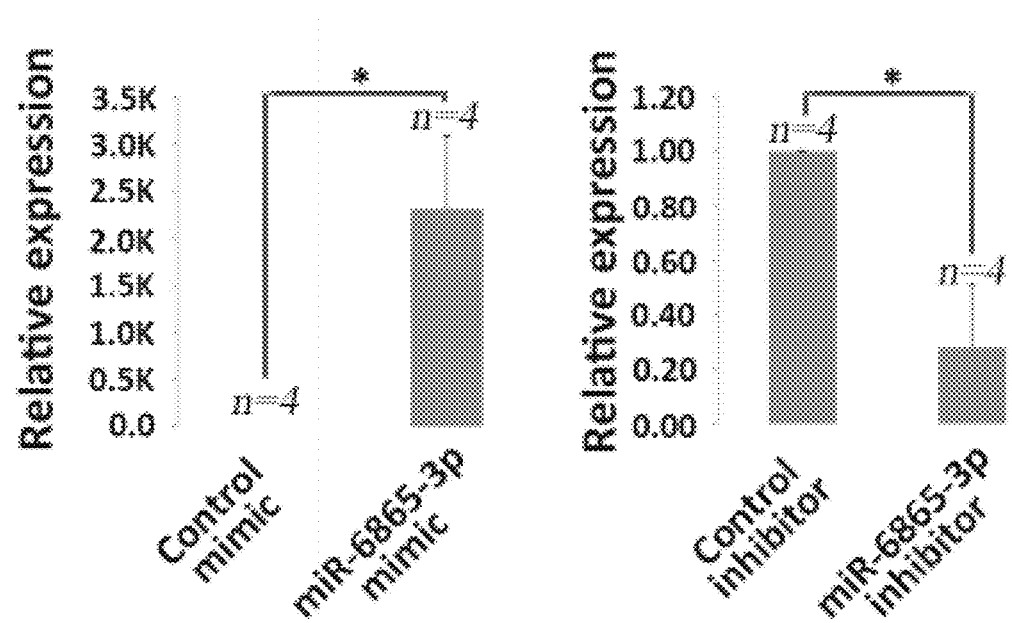

Analysis of hsa-miR-335-5p, hsa-miR-3613-3p and hsa-miR-6865-3p targets using multiple bioinformatics tools show that among others, LRRK2 and Parkin are predicted targets of hsa-miR-335-5p, and SNCA is a predicted target of hsa-miR-3613-3p. The regulation of LRRK2 expression in SHSY-5Y cells as a result of modulation in hsa-miR-335-5p levels was confirmed by western blot analysis. hsa-miR-335-5p was overexpressed (FIG. 6A) and inhibited (FIG. 6A) using mimic and antagomir of hsa-miR-335-5p transfected into neuroblastoma cells. The cells were lysed after 48 hours post-transfection and used for western blot analysis. hsa-miR-335-5p mimic showed downregulation of LRRK2 and hsa-miR-335-5p antagomir showed upregulation of LRRK2 (FIG. 6B, C). The hsa-miR-3613-3p regulated SNCA expression in SH-SY5Y cells in moderation. A similar experimental approach like hsa-miR-335-5p was adopted for hsa-miR-3613-3p (FIG. 6D) and the results showed moderate SNCA upregulation with hsa-miR-3613-3p mimic and a moderate SNCA downregulation with hsa-miR-3613-3p antagomir at protein level (FIG. 6E, F) and transcript level (FIG. 6G).

The target discovery using LC-MS was performed to find novel targets for hsa-miR-335-5p, hsa-miR-3613-3p and hsa-miR-6865-3p.

a. The proteins with differential expression pattern as a result of hsa-miR-335-5p modulation include acadsb, slc4a7, lnp/kiaa1715, supt5h, sdhd. Wdr1, cmpk1, slc25a1, hmgcs1, twf2, ppp1r18, exoc8, tm9sf4, kif16b, dnajc2, sel11, hectd1, gmppb.

b. The proteins with differential expression pattern as a result of hsa-miR-3613-3p modulation include wdr1, gmppb, hmbs, em14, hebp1, apmap/c20orf3, sord, pcyt2, stat3, top2a, skiv2l2, cdc20, myole, ttll12, atad2, carm1, arfgap1, ppp4r1, nde1/ndel1.

c. The proteins with differential expression pattern as a result of hsa-miR-6865-3p modulation include wdr1, ppp1r18, ppp4r1, ube2h, ube3c, stx16, ube4h, gtf2f1, map1b, ube2a, dusp3, arhgap1, nsun2, acox1, fkbp10, fam107b, pofut1, tomm22, hspb8, sbds.

Example 13

Measurement of levels of a combination of two or more miRNAs in serum from patients can assist in distinctly differentiating between a potential PD patient and a healthy individual. A serum sample is obtained from blood withdrawn from patients suspected of PD. The serum is used for total microRNA isolation and enrichment. This RNA would then be tested using qPCR to measure the levels of any two or more of the 85 miRNAs mentioned in Example 1, or any one of three miRNAs mentioned in Examples 5-7. Detectable levels of any two or more of the 85 miRNAs or any one of the three miRNAs confirms the patient has PD. If desired, other sample fluids may be utilized, including plasma, venous or arterial blood, or CSF samples withdrawn by lumbar puncture. Such plasma, blood or CSF samples are processed as above. It will be understood that measurement of more than two miRNAs in combination or a set of combinations used in a test matrix may desirably increase the accuracy of PD diagnosis.

Example 14

Since a combination of miRNA can be used for diagnosis it may be advisable to test all the candidates to eliminate any cohort-based variation. It is understood that any detectable amounts of relevant miRNA will indicate PD pathology. However, those of ordinary skill in the art recognize it may be clinically helpful to use values of 164 v 182 samples to set an artificial threshold for diagnosis. Differential miRNA levels can be used to develop diagnostic biomarker kits that can be used by clinicians in diagnosis as well as in clinical trials. In this study the presence and quantification of miRNA from serum was determined by qRT-PCR which amplifies and quantifies the RNA is question. Other suitable techniques known to those of ordinary skill herein may be alternatively utilized, including use of labeled antisense sequences and labeled antibodies. Suitable antibodies are preferentially selective, referring to a binding reaction between two molecules that is typically more than 10 to 100 times background molecular associations under measurement conditions. Thus, under designated immunoassay conditions, the specified antibodies bind to a particular miRNA sequence, thereby identifying its presence. Specific binding to an antibody under such conditions requires an antibody that is selected for its specificity for a particular miRNA. For example, antibodies raised against a particular miRNA can be selected by subtracting out antibodies that cross-react with other molecules. A variety of immunoassay formats may be used to select antibodies specifically immunoreactive with a particular miRNA including solid-phase ELISA immunoassays (see, e.g., Harlow & Lane, Antibodies, A Laboratory Manual (1988) for a description of immunoassay formats and conditions that can be used to determine specific immunoreactivity). Methods for determining whether two molecules specifically interact are disclosed therein, and methods of determining binding affinity and specificity are well known in the art (see, for example, Harlow and Lane, Antibodies: A laboratory manual (Cold Spring Harbor Laboratory Press, 1988); Friefelder, "Physical Biochemistry: Applications to biochemistry and molecular biology" (W.H. Freeman and Co. 1976)). The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')2, Fab, Fv and rIgG). See also, Pierce Catalog and Handbook, 1994-1995 (Pierce Chemical Co., Rockford, Ill.). See also, e.g., Kuby, J., Immunology, 3rd Ed., W.H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science, Vol. 246 (1989) 1275-81. These and other methods of making, for example, chimeric, humanized, CDR-grafted, single chain, and bifunctional antibodies are well known to those skilled in the art (Winter and Harris, Immunol. Today, Vol. 14 (1993) 243-46; Ward et al., Nature, Vol. 341 (1989) 544-46; Harlow and Lane, supra, 1988; Hilyard et al., Protein Engineering: A practical approach (IRL Press 1992); Borrabeck, Antibody Engineering, 2d ed. (Oxford University Press 1995). Methods for producing both monoclonal and polyclonal antibodies from identified RNA sequences are well known in the art.

Example 15

Many neurodegenerative diseases are closely related to each other when it comes to symptoms as well as pathological markers. The circulating diagnostic markers for one neurodegenerative disease can be useful for diagnosis of other disease. A method to diagnose other neurodegenerative diseases like Dementia with Lewy body (DLB), Amyotrophic lateral sclerosis (ALS), Alzheimer's disease (AD), Multiple system atrophy (MSA), CorticoBasal Degeneration (CBD), Progressive Supranuclear Palsy (PSP) can also be developed using similar miRNA measurements of candidates mentioned above. Disease specific kits can be developed similar to one mentioned in [0037] with various combinations of miRNAs listed in [0019].

Example 16

The miRNAs detected in one or more combinations can regulate several proteins in the cells. Novel protein targets for PD can be discovered using these microRNAs and their combinations. The involvement of these proteins in PD etiology can be further established to target them for therapy.

Example 17

We have experimentally confirmed the predicted regulation of LRRK2 by hsa-miR-335-5p and SNCA by hsa-miR-3613-3p in dopaminergic neuronal cell lines. Therapeutic intervention to regulate the novel targets mentioned can be achieved by RNA interference technologies.

Example 18

Small nucleic acid molecules derived from miRNAs mentioned in [0019] will be designed to therapeutically intervene by specifically targeting genes in PD brains to achieve complete or partial remedy. The effects shown in [0040] will be achieved for precise targeting in brain cells.

What is claimed is:

1. A method, comprising the steps of:
   obtaining a sample of a kind selected from the group consisting of whole blood, CSF, plasma, serum and saliva from a human patient;
   determining differential levels of each of SEQ ID NOS: 22, 25 and 77 within said sample compared to levels in a sample of the same kind from a healthy control;
   correlating differential levels of at least 1.2 fold above that of the healthy control for each of SEQ ID NOS: 22, 25 and 77 to a disease state of Parkinson's disease in said human patient; and
   administering treatment for Parkinson's disease to said human patient, wherein
   said treatment comprises administering L-dopa, peripheral decarboxylase inhibitor, dopamine agonist, catechol-O-methyltransferase inhibitor, amantadine or an MAO-B inhibitor to said patient.

2. The method of claim 1, wherein said sample is serum, plasma or whole blood.

3. The method according to claim 1, wherein the differential level of SEQ ID NOS: 22, 25 and 77 is identified using qRT-PCR.

4. The method according to claim 1, wherein the differential level of SEQ ID NOS: 22, 25 and 77 is identified using labeled antisense nucleotide sequences.

5. The method according to claim 1, wherein the presence of SEQ ID NOS: 22, 25 and 77 is determined using microarray profiling.

6. The method according to claim 1, wherein the presence of SEQ ID NOS: 22, 25 and 77 is determined using high throughput NGS sequencing.

* * * * *

SEQUENCE LISTING

<160> NUMBER OF SEQ ID NOS: 88

<210> SEQ ID NO 1
<211> LENGTH: 22
<212> TYPE: RNA
<213> ORGANISM: Homo sapien

<400> SEQUENCE: 1
ucaccgggug uaaaucagcu ug                                          22

<210> SEQ ID NO 2
<211> LENGTH: 79
<212> TYPE: RNA
<213> ORGANISM: Homo sapien

<400> SEQUENCE: 2
cccgggcuga gguaggaggu uguauaguug aggaggacac ccaaggagau cacuauacgg     60
ccuccuagcu uuccccagg                                                 79

<210> SEQ ID NO 3
<211> LENGTH: 23
<212> TYPE: RNA
<213> ORGANISM: Homo sapien

<400> SEQUENCE: 3

-continued

```
ccugcagcga cuugauggcu ucc                                              23

<210> SEQ ID NO 4
<211> LENGTH: 111
<212> TYPE: RNA
<213> ORGANISM: Homo sapien

<400> SEQUENCE: 4
ccacgguccu aguuaaaaag gcacauuccu agacccugcc ucagaacuac ugaacagagu      60 cacuggugu ggaguccagg aaucugcauu uuuacccua ucgccccgc c                 111

<210> SEQ ID NO 5
<211> LENGTH: 22
<212> TYPE: RNA
<213> ORGANISM: Homo sapien

<400> SEQUENCE: 5
ucaaaacuga ggggcauuuu cu                                               22

<210> SEQ ID NO 6
<211> LENGTH: 22
<212> TYPE: RNA
<213> ORGANISM: Homo sapien

<400> SEQUENCE: 6
gcuauuucac gacaccaggg uu                                               22

<210> SEQ ID NO 7
<211> LENGTH: 22
<212> TYPE: RNA
<213> ORGANISM: Homo sapien

<400> SEQUENCE: 7
cuccuacaua uuagcauuaa ca                                               22

<210> SEQ ID NO 8
<211> LENGTH: 22
<212> TYPE: RNA
<213> ORGANISM: Homo sapien

<400> SEQUENCE: 8
ccaauauuac ugugcugcuu ua                                               22

<210> SEQ ID NO 9
<211> LENGTH: 23
<212> TYPE: RNA
<213> ORGANISM: Homo sapien

<400> SEQUENCE: 9
aacauucauu gcugucggug ggu                                              23

<210> SEQ ID NO 10
<211> LENGTH: 21
<212> TYPE: RNA
<213> ORGANISM: Homo sapien

<400> SEQUENCE: 10
cuauauauca aacauauucc u                                                21

<210> SEQ ID NO 11
<211> LENGTH: 21
<212> TYPE: RNA
```

<213> ORGANISM: Homo sapien

<400> SEQUENCE: 11
augaccuaug aauugacaga c                                            21

<210> SEQ ID NO 12
<211> LENGTH: 22
<212> TYPE: RNA
<213> ORGANISM: Homo sapien

<400> SEQUENCE: 12
accuggcaua caauguagau uu                                           22

<210> SEQ ID NO 13
<211> LENGTH: 24
<212> TYPE: RNA
<213> ORGANISM: Homo sapien

<400> SEQUENCE: 13
agcgcgggcu gagcgcugcc aguc                                         24

<210> SEQ ID NO 14
<211> LENGTH: 21
<212> TYPE: RNA
<213> ORGANISM: Homo sapien

<400> SEQUENCE: 14
auccccagau acaauggaca a                                            21

<210> SEQ ID NO 15
<211> LENGTH: 22
<212> TYPE: RNA
<213> ORGANISM: Homo sapien

<400> SEQUENCE: 15
ugguuuaccg ucccacauac au                                           22

<210> SEQ ID NO 16
<211> LENGTH: 23
<212> TYPE: RNA
<213> ORGANISM: Homo sapien

<400> SEQUENCE: 16
cugacugaau agguagdgguc auu                                         23

<210> SEQ ID NO 17
<211> LENGTH: 86
<212> TYPE: RNA
<213> ORGANISM: Homo sapien

<400> SEQUENCE: 17
gagggaaagc aggccaaccu cgaggaucuc cccagccuug gcguucaggu gcugaggaga    60
ucgucgaggu uggccugcuu ccccuc                                       86

<210> SEQ ID NO 18
<211> LENGTH: 85
<212> TYPE: RNA
<213> ORGANISM: Homo sapien

<400> SEQUENCE: 18
ggaccugccc ugggcuuucu agucucagcu cuccuccagc ucagcugguc aggagagcug    60
agacuagaaa gcccagggca gguuc                                        85

```
<210> SEQ ID NO 19
<211> LENGTH: 81
<212> TYPE: RNA
<213> ORGANISM: Homo sapien

<400> SEQUENCE: 19
accugcccug ggcuuucuag ucucagcucu ccugaccagc ugagcuggag gagagcugag    60
acuagaaagc ccagggcagg u                                              81

<210> SEQ ID NO 20
<211> LENGTH: 85
<212> TYPE: RNA
<213> ORGANISM: Homo sapien

<400> SEQUENCE: 20
ggcgccuccu gcucugcugu gccgccaggg ccuccccuag cgcgccuucu ggagaggcuu    60
ugugcggaua cggggcugga ggccu                                          85

<210> SEQ ID NO 21
<211> LENGTH: 79
<212> TYPE: RNA
<213> ORGANISM: Homo sapien

<400> SEQUENCE: 21
aauuaauccc ucucuuucua guucuuccua gagugaggaa aagcuggguu gagagggcaa    60
acaaauuaac uaauuaauu                                                 79

<210> SEQ ID NO 22
<211> LENGTH: 23
<212> TYPE: RNA
<213> ORGANISM: Homo sapien

<400> SEQUENCE: 22
ucaagagcaa uaacgaaaaa ugu                                            23

<210> SEQ ID NO 23
<211> LENGTH: 98
<212> TYPE: RNA
<213> ORGANISM: Homo sapien

<400> SEQUENCE: 23
acccaaaccc uaggucugcu gacuccuagu ccagggcucg ugauggcugg ugggcccuga    60
acgagggguc uggaggccug gguuugaaua ucgacagc                            98

<210> SEQ ID NO 24
<211> LENGTH: 23
<212> TYPE: RNA
<213> ORGANISM: Homo sapien

<400> SEQUENCE: 24
uaggcagugu cauuagcuga uug                                            23

<210> SEQ ID NO 25
<211> LENGTH: 24
<212> TYPE: RNA
<213> ORGANISM: Homo sapien

<400> SEQUENCE: 25
acaaaaaaaa aagcccaacc cuuc                                           24
```

```
<210> SEQ ID NO 26
<211> LENGTH: 92
<212> TYPE: RNA
<213> ORGANISM: Homo sapien

<400> SEQUENCE: 26
ugucacuccg ccagcaucau gaagugcacu caugauaugu uugccccauc agcgugucac      60
gagggcauuu caugaugcag gcgggguugg ca                                    92

<210> SEQ ID NO 27
<211> LENGTH: 22
<212> TYPE: RNA
<213> ORGANISM: Homo sapien

<400> SEQUENCE: 27
cugggaggug ugauaucgug gu                                               22

<210> SEQ ID NO 28
<211> LENGTH: 19
<212> TYPE: RNA
<213> ORGANISM: Homo sapien

<400> SEQUENCE: 28
acuggacuug gaggcagaa                                                   19

<210> SEQ ID NO 29
<211> LENGTH: 111
<212> TYPE: RNA
<213> ORGANISM: Homo sapien

<400> SEQUENCE: 29
cuuuugcugu caguuuucu guugcuuguc uugguuuuau gccuuuaua ucaaggcaca        60 uaaaaggcau aaaccaaga caagcaacaa aaaaggauu gaucacagaa g                 111

<210> SEQ ID NO 30
<211> LENGTH: 22
<212> TYPE: RNA
<213> ORGANISM: Homo sapien

<400> SEQUENCE: 30
ucaggugugg aaacugaggc ag                                               22

<210> SEQ ID NO 31
<211> LENGTH: 17
<212> TYPE: RNA
<213> ORGANISM: Homo sapien

<400> SEQUENCE: 31
uggagagaaa ggcagua                                                     17

<210> SEQ ID NO 32
<211> LENGTH: 20
<212> TYPE: RNA
<213> ORGANISM: Homo sapien

<400> SEQUENCE: 32
agcccccugg ccccaaaccc                                                  20

<210> SEQ ID NO 33
<211> LENGTH: 18
<212> TYPE: RNA
<213> ORGANISM: Homo sapien
```

```
<400> SEQUENCE: 33
uugcacuugu cucaguga                                              18

<210> SEQ ID NO 34
<211> LENGTH: 94
<212> TYPE: RNA
<213> ORGANISM: Homo sapien

<400> SEQUENCE: 34
ugguuugcga cucugaaaac uagaagguuu augacugggc auuucucacc caaugcccaa    60
uauugaacuu ucuaguuguc agagucauua accc                                94

<210> SEQ ID NO 35
<211> LENGTH: 70
<212> TYPE: RNA
<213> ORGANISM: Homo sapien

<400> SEQUENCE: 35
uuccugcaga auuguuucuuu ugccgugcaa guuuaaguuu uugcacggca aaagaaacaa   60
uccagagggu                                                           70

<210> SEQ ID NO 36
<211> LENGTH: 73
<212> TYPE: RNA
<213> ORGANISM: Homo sapien

<400> SEQUENCE: 36 acugccuuc agccagagcu ggcugaaggg cagaagggaa cuguccuuca gccagagcug    60
gcugaagggc aga                                                      73

<210> SEQ ID NO 37
<211> LENGTH: 22
<212> TYPE: RNA
<213> ORGANISM: Homo sapien

<400> SEQUENCE: 37
uuuugcaaua uguuccugaa ua                                            22

<210> SEQ ID NO 38
<211> LENGTH: 21
<212> TYPE: RNA
<213> ORGANISM: Homo sapien

<400> SEQUENCE: 38
gcaguccaug ggcauauaca c                                             21

<210> SEQ ID NO 39
<211> LENGTH: 81
<212> TYPE: RNA
<213> ORGANISM: Homo sapien

<400> SEQUENCE: 39
ggcugcuucu cgccucuguc cagcugugug gccuuggaca agccucuugg uuacacagcu   60
ggacagaggc acgaaacagc c                                             81

<210> SEQ ID NO 40
<211> LENGTH: 26
<212> TYPE: RNA
<213> ORGANISM: Homo sapien
```

```
<400> SEQUENCE: 40
cccagggcuu ggaguggggc aagguu                                          26

<210> SEQ ID NO 41
<211> LENGTH: 22
<212> TYPE: RNA
<213> ORGANISM: Homo sapien

<400> SEQUENCE: 41
agcaaggcgg caucucucug au                                              22

<210> SEQ ID NO 42
<211> LENGTH: 22
<212> TYPE: RNA
<213> ORGANISM: Homo sapien

<400> SEQUENCE: 42
ugcggggaca ggccagggca uc                                              22

<210> SEQ ID NO 43
<211> LENGTH: 22
<212> TYPE: RNA
<213> ORGANISM: Homo sapien

<400> SEQUENCE: 43
ucugccaucc ucccuccccu ac                                              22

<210> SEQ ID NO 44
<211> LENGTH: 21
<212> TYPE: RNA
<213> ORGANISM: Homo sapien

<400> SEQUENCE: 44
agcagacuug accuacaauu a                                               21

<210> SEQ ID NO 45
<211> LENGTH: 80
<212> TYPE: RNA
<213> ORGANISM: Homo sapien

<400> SEQUENCE: 45
aaugaaggau uacggaccag cuaagggagg cauuaggauc cuuauucuug ccucccuuag      60
uuggucccua auccuucguu                                                 80

<210> SEQ ID NO 46
<211> LENGTH: 18
<212> TYPE: RNA
<213> ORGANISM: Homo sapien

<400> SEQUENCE: 46
uggauaugau gacugaaa                                                   18

<210> SEQ ID NO 47
<211> LENGTH: 21
<212> TYPE: RNA
<213> ORGANISM: Homo sapien

<400> SEQUENCE: 47
gacagagugc cacuuacuga a                                               21

<210> SEQ ID NO 48
<211> LENGTH: 22
```

```
<212> TYPE: RNA
<213> ORGANISM: Homo sapien

<400> SEQUENCE: 48
augcaccugg gcaaggauuc ug                                              22

<210> SEQ ID NO 49
<211> LENGTH: 22
<212> TYPE: RNA
<213> ORGANISM: Homo sapien

<400> SEQUENCE: 49
ugauugguac gucuguggu ag                                               22

<210> SEQ ID NO 50
<211> LENGTH: 22
<212> TYPE: RNA
<213> ORGANISM: Homo sapien

<400> SEQUENCE: 50
uacucaggag aguggcaauc ac                                              22

<210> SEQ ID NO 51
<211> LENGTH: 21
<212> TYPE: RNA
<213> ORGANISM: Homo sapien

<400> SEQUENCE: 51
cuccagaggg aaguacuuuc u                                               21

<210> SEQ ID NO 52
<211> LENGTH: 90
<212> TYPE: RNA
<213> ORGANISM: Homo sapien

<400> SEQUENCE: 52
ucccaugcug ugacccucua gaggaagcac uuucuguuug uugucugaga aaaacaaag      60 ugcuucccuu uagaguguua ccguuuggga                                      90

<210> SEQ ID NO 53
<211> LENGTH: 88
<212> TYPE: RNA
<213> ORGANISM: Homo sapien

<400> SEQUENCE: 53
ucccaugcug ugacccucua gaggaagcac uuucuguuug uugucugaga aaaacaaag      60 ugcuucccuu uagaguuacu guuuggga                                        88

<210> SEQ ID NO 54
<211> LENGTH: 91
<212> TYPE: RNA
<213> ORGANISM: Homo sapien

<400> SEQUENCE: 54
cgacuugcuu ucucuccucc augccuugag uguaggaccg uuggcaucuu aauuaccuc      60 ccacacccaa ggcuugcaga agagcgagcc u                                    91

<210> SEQ ID NO 55
<211> LENGTH: 25
<212> TYPE: RNA
<213> ORGANISM: Homo sapien
```

```
<400> SEQUENCE: 55
aaaaaccaca auuacuuug cacca                                      25

<210> SEQ ID NO 56
<211> LENGTH: 22
<212> TYPE: RNA
<213> ORGANISM: Homo sapien

<400> SEQUENCE: 56
caaaaaccgg caauuacuuu ug                                        22

<210> SEQ ID NO 57
<211> LENGTH: 21
<212> TYPE: RNA
<213> ORGANISM: Homo sapien

<400> SEQUENCE: 57
caaaaacugc aauuacuuuc a                                         21

<210> SEQ ID NO 58
<211> LENGTH: 21
<212> TYPE: RNA
<213> ORGANISM: Homo sapien

<400> SEQUENCE: 58
aaagguaauu gugguuucug c                                         21

<210> SEQ ID NO 59
<211> LENGTH: 21
<212> TYPE: RNA
<213> ORGANISM: Homo sapien

<400> SEQUENCE: 59
uaaaaacugc aauuacuuuu a                                         21

<210> SEQ ID NO 60
<211> LENGTH: 19
<212> TYPE: RNA
<213> ORGANISM: Homo sapien

<400> SEQUENCE: 60
aaaaaccaca auuacuuuu                                            19

<210> SEQ ID NO 61
<211> LENGTH: 54
<212> TYPE: RNA
<213> ORGANISM: Homo sapien

<400> SEQUENCE: 61
aaaaguaauu gcgguuuuug cuauuggouuu uaauggcagu acuuuugca ccag      54

<210> SEQ ID NO 62
<211> LENGTH: 22
<212> TYPE: RNA
<213> ORGANISM: Homo sapien

<400> SEQUENCE: 62
aaaaguacuu gcggauuuug cu                                        22

<210> SEQ ID NO 63
<211> LENGTH: 25
<212> TYPE: RNA
<213> ORGANISM: Homo sapien
```

-continued

```
<400> SEQUENCE: 63
aaaaaccaca auuacuuuug cacca                                          25

<210> SEQ ID NO 64
<211> LENGTH: 20
<212> TYPE: RNA
<213> ORGANISM: Homo sapien

<400> SEQUENCE: 64
uaaaaacugc aauuacuuuc                                                20

<210> SEQ ID NO 65
<211> LENGTH: 110
<212> TYPE: RNA
<213> ORGANISM: Homo sapien

<400> SEQUENCE: 65
gccuaaacua uuagguuggu gcaaaaguaa ucacuguuuu ugccauuacu cucaguggca    60
aaaaccguga uuacuuuugc accaaccuag uaacaccuuc acugggggg               110

<210> SEQ ID NO 66
<211> LENGTH: 97
<212> TYPE: RNA
<213> ORGANISM: Homo sapien

<400> SEQUENCE: 66
cuucauccac caguccucca ggaacaucaa ggaucuuaaa cuuugccaga gcuacaaagg    60
caaaguuuaa gauccuugaa guuccugggg gaaccau                             97

<210> SEQ ID NO 67
<211> LENGTH: 22
<212> TYPE: RNA
<213> ORGANISM: Homo sapien

<400> SEQUENCE: 67
cacacacugc aauuacuuuu gc                                             22

<210> SEQ ID NO 68
<211> LENGTH: 21
<212> TYPE: RNA
<213> ORGANISM: Homo sapien

<400> SEQUENCE: 68
aaacuacuga aaaucaaaga u                                              21

<210> SEQ ID NO 69
<211> LENGTH: 95
<212> TYPE: RNA
<213> ORGANISM: Homo sapien

<400> SEQUENCE: 69
gacaccacau gcuccuccag gccugccugc ccuccagguc auguccagu gucccacaga    60 ugcagcacca cggcccaggc ggcauuggug ucacc                               95

<210> SEQ ID NO 70
<211> LENGTH: 97
<212> TYPE: RNA
<213> ORGANISM: Homo sapien

<400> SEQUENCE: 70
```
ccaccacggu gcuggcacca gggccucugc cccguaggac accgaggcuu augaauagga    60
gcagugccgg ccaaggcgcc ggcaccaucu uggugau                            97

<210> SEQ ID NO 71
<211> LENGTH: 22
<212> TYPE: RNA
<213> ORGANISM: Homo sapien

<400> SEQUENCE: 71
ugggaaagag aaagaacaag ua                                            22

<210> SEQ ID NO 72
<211> LENGTH: 22
<212> TYPE: RNA
<213> ORGANISM: Homo sapien

<400> SEQUENCE: 72
ucgggccugg gguugggga gc                                             22

<210> SEQ ID NO 73
<211> LENGTH: 59
<212> TYPE: RNA
<213> ORGANISM: Homo sapien

<400> SEQUENCE: 73
cgggcucugg gugcaguggg gguucccacg ccgcggcaac caccacuguc ucccccag     59

<210> SEQ ID NO 74
<211> LENGTH: 25
<212> TYPE: RNA
<213> ORGANISM: Homo sapien

<400> SEQUENCE: 74 uaggggugggg ggaauucagg ggugu                                        25

<210> SEQ ID NO 75
<211> LENGTH: 20
<212> TYPE: RNA
<213> ORGANISM: Homo sapien

<400> SEQUENCE: 75
uccccaaccc cugcccgcag                                               20

<210> SEQ ID NO 76
<211> LENGTH: 61
<212> TYPE: RNA
<213> ORGANISM: Homo sapien

<400> SEQUENCE: 76
gugcggaacg cuggccgggg cgggagggga agggacgccc ggccggaacg ccgcacucac   60
g                                                                   61

<210> SEQ ID NO 77
<211> LENGTH: 21
<212> TYPE: RNA
<213> ORGANISM: Homo sapien

<400> SEQUENCE: 77
acacccucuu ucccuaccgc c                                             21

<210> SEQ ID NO 78
<211> LENGTH: 22

```
<212> TYPE: RNA
<213> ORGANISM: Homo sapien

<400> SEQUENCE: 78
cagagggaau acagagggca au                                              22

<210> SEQ ID NO 79
<211> LENGTH: 67
<212> TYPE: RNA
<213> ORGANISM: Homo sapien

<400> SEQUENCE: 79
uggagcugug ugcagggcca gcgcggagcc cgagcagccg cggugaagcg ccugugcucu     60
gccgaga                                                               67

<210> SEQ ID NO 80
<211> LENGTH: 20
<212> TYPE: RNA
<213> ORGANISM: Homo sapien

<400> SEQUENCE: 80
ugugacccua gaauaauuac                                                 20

<210> SEQ ID NO 81
<211> LENGTH: 22
<212> TYPE: RNA
<213> ORGANISM: Homo sapien

<400> SEQUENCE: 81
cgggacugua gagggcauga gc                                              22

<210> SEQ ID NO 82
<211> LENGTH: 80
<212> TYPE: RNA
<213> ORGANISM: Homo sapien

<400> SEQUENCE: 82
ccuugcugau ggcagauguc ggaucugccu cgcuuauacg ugcccuugcu gauggcagau     60
gucgggucug ccucgcuuau                                                 80

<210> SEQ ID NO 83
<211> LENGTH: 82
<212> TYPE: RNA
<213> ORGANISM: Homo sapien

<400> SEQUENCE: 83
aaggagcacu cacuccaauu ucccuggacu gggggcaggc ugccaccucc uggggacagg     60
ggauuggggc aggauguucc ag                                              82

<210> SEQ ID NO 84
<211> LENGTH: 77
<212> TYPE: RNA
<213> ORGANISM: Homo sapien

<400> SEQUENCE: 84
ugcaaugccc uacucagaaa ggugccauuu auguagauuu uaugucacug gcuccuuucu     60
ggguagagca aggcuca                                                    77

<210> SEQ ID NO 85
<211> LENGTH: 22
<212> TYPE: RNA
```

```
<213> ORGANISM: Homo sapien

<400> SEQUENCE: 85
acaguagagg gaggaaucgc ag                                              22

<210> SEQ ID NO 86
<211> LENGTH: 20
<212> TYPE: RNA
<213> ORGANISM: Homo sapien

<400> SEQUENCE: 86
gugagucagg gugggggcugg                                                20

<210> SEQ ID NO 87
<211> LENGTH: 69
<212> TYPE: RNA
<213> ORGANISM: Homo sapien

<400> SEQUENCE: 87
agaggcuugg gccgccgagc uggacccgga ccgguuuugg guacuguacu gggggcaggg     60
cagagaggg                                                             69

<210> SEQ ID NO 88
<211> LENGTH: 106
<212> TYPE: RNA
<213> ORGANISM: Homo sapien

<400> SEQUENCE: 88
gugcucgcuu cggcagcaca uauacuaaaa uuggaacgau acagagaaga uuagcauggc     60
cccugcgcaa ggaugacacg caaauucgug aagcguucca uauuuu                   106
```